United States Patent
Shinano et al.

(10) Patent No.: US 8,057,701 B2
(45) Date of Patent: Nov. 15, 2011

(54) TRIFUNCTIONAL (METH)ACRYLATE COMPOUND AND POLYMERIZABLE COMPOSITION CONTAINING SAME

(75) Inventors: Hirokatsu Shinano, Tokyo (JP); Satoshi Yanagisawa, Tokyo (JP); Masatomi Irisawa, Tokyo (JP); Kazuyuki Itano, Tokyo (JP)

(73) Assignee: Adeka Corporation, Tokyo (JP)

( * ) Notice: Subject to any disclaimer, the term of this patent is extended or adjusted under 35 U.S.C. 154(b) by 0 days.

(21) Appl. No.: 12/808,594

(22) PCT Filed: Mar. 10, 2009

(86) PCT No.: PCT/JP2009/054562
§ 371 (c)(1), (2), (4) Date: Jun. 16, 2010

(87) PCT Pub. No.: WO2009/122868
PCT Pub. Date: Oct. 8, 2009

(65) Prior Publication Data
US 2011/0037025 A1    Feb. 17, 2011

(30) Foreign Application Priority Data
Apr. 1, 2008 (JP) .................................. 2008-095563

(51) Int. Cl.
C09K 19/00 (2006.01)
C09K 19/06 (2006.01)
C09K 19/32 (2006.01)
C09K 19/52 (2006.01)

(52) U.S. Cl. ........... 252/299.6; 252/299.01; 252/299.61; 252/299.62; 428/1.1; 430/20; 560/56; 560/73

(58) Field of Classification Search ............ 252/299.01, 252/299.6, 299.61, 299.62; 428/1.1; 430/20; 560/56, 73
See application file for complete search history.

(56) References Cited

U.S. PATENT DOCUMENTS
2007/0228326 A1    10/2007    Goldfinger et al.

FOREIGN PATENT DOCUMENTS

| JP | 2000-178233 | 6/2000 |
|---|---|---|
| JP | 2003-321430 | 11/2003 |
| JP | 2004-043710 | 2/2004 |
| JP | 2004-059772 | 2/2004 |
| JP | 2005-309255 | 11/2005 |
| JP | 2007-119415 | 5/2007 |
| WO | 2006/049111 | 5/2006 |
| WO | WO 2007/120458 | 10/2007 |

OTHER PUBLICATIONS

International Search Report, PCT/JP2009/054562, May 26, 2009.

Primary Examiner — Geraldina Visconti
(74) Attorney, Agent, or Firm — Young & Thompson

(57) ABSTRACT

A trifunctional (meth)acrylate compound of general formula (I) is provided

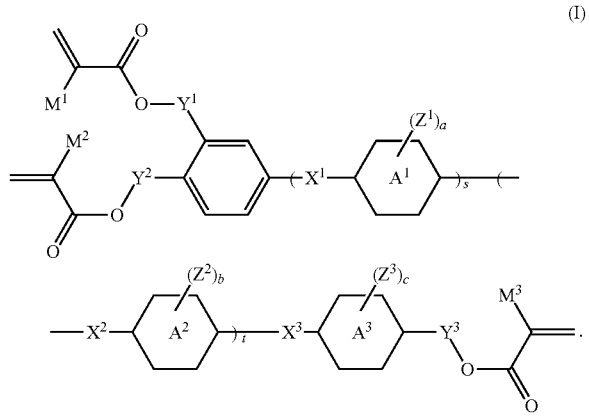

The compound is capable of retaining a liquid crystal phase at or below 30 ° C. Polymerizable compositions containing a compound of formula (I) are also provided.

20 Claims, 1 Drawing Sheet

Cr:Crystal phase, N:Nematic phase, I:Isotropic liquid

Cr:Crystal phase, N:Nematic phase, I:Isotropic liquid

Cr:Crystal phase, N:Nematic phase

TRIFUNCTIONAL (METH)ACRYLATE COMPOUND AND POLYMERIZABLE COMPOSITION CONTAINING SAME

TECHNICAL FIELD

This invention relates to a novel trifunctional (meth)acrylate compound having at least one fused ring. A polymerizable composition containing the compound exhibits excellent heat resistance, hardness, optical characteristics, and solvent resistance. An optically anisotropic material obtained by photopolymerizing the polymerizable composition is useful as an optical material providing, for example, a retardation film, a polarizer, a polarizing prism, or an optical film for display devices.

BACKGROUND ART

Liquid crystals are applied to display media in which the reversible movement of liquid crystal molecules is made use of, such as display devices typically of TN or STN mode. Besides the application to display media, liquid crystals have been studied for applicability to optically anisotropic elements, such as a retardation film, a polarizer, a polarizing prism, a luminance-improving film, a low pass filter, and various optical filters, taking advantage of their anisotropy in physical properties, such as refractive index, dielectric constant, magnetic susceptibility, elastic modulus, and thermal expansion coefficient, as well as their aligning properties.

The above described optically anisotropic elements are obtained by, for example, uniformly aligning the molecules of a liquid crystal compound having a polymerizable functional group or a polymerizable composition containing the liquid crystal compound into a liquid crystal state and irradiating the compound or the composition while being in the liquid crystal state with energy rays, such as ultraviolet rays, to cause photopolymerization. It is required to fix the aligned state of the liquid crystal compound uniformly and semi-permanently.

When the polymerizable composition has a high liquid crystal phase temperature, photopolymerization induced by energy rays may be unintentionally accompanied by thermal polymerization, which will disturb the uniform alignment of the liquid crystal molecules, making it difficult to fix a desired state of alignment. In order to facilitate temperature control during cure, a polymerizable composition showing a liquid crystal phase at or near room temperature has been demanded.

A polymer film is obtained by polymerizing a polymerizable composition in the form of coating film applied to a substrate. If the composition contains a non-polymerizable compound, the resulting polymer film may have insufficient strength or contain residual stress-induced strain. Removing a non-polymerizable compound using, e.g., a solvent can result in a failure to retain film homogeneity and cause unevenness. To obtain a polymer film with a uniform thickness, it is therefore preferred to apply a polymerizable composition in the form of a solution in a solvent to a substrate. Hence, it is desirable for a liquid crystal compound or a polymerizable composition containing it to have good solubility in a solvent.

The above discussed optically anisotropic element is usually used not as a single film but as stacked on a substrate, such as glass, together with other functional material and is therefore required to have solvent resistance and high hardness so as not to interfere with applying the other functional material.

Polymerizable compounds having a (meth)acrylic group as a polymerizable functional group have been extensively studied for use as a monomer providing an optically anisotropic element because they exhibit high polymerization reactivity and produce highly transparent polymers. Inter alia, bifunctional or trifunctional monomers having two or three (meth) acrylic groups are known to be an effective means for providing polymers with improved heat resistance and solvent resistance. For example, patent documents 1 to 6 below propose trifunctional monomers. However, the problem with these monomers is that the resulting polymers can suffer from crystallization or be difficult to control to provide uniform molecular alignment.

Patent document 1: JP 2000-178233A
Patent document 2: JP 2004-043710A
Patent document 3: JP 2003-321430A
Patent document 4: JP 2004-059772A
Patent document 5: JP 2005-309255A
Patent document 6: WO2006/049111

DISCLOSURE OF THE INVENTION

Problem to be Solved by the Invention

An object of the present invention is to provide a polymerizable compound and a polymerizable composition which are controllable in molecular alignment and provide polymers having good heat resistance and optical characteristics.

Means for Solving the Problem

The invention provides a trifunctional (meth)acrylate compound represented by general formula (I):

[Formula 1]

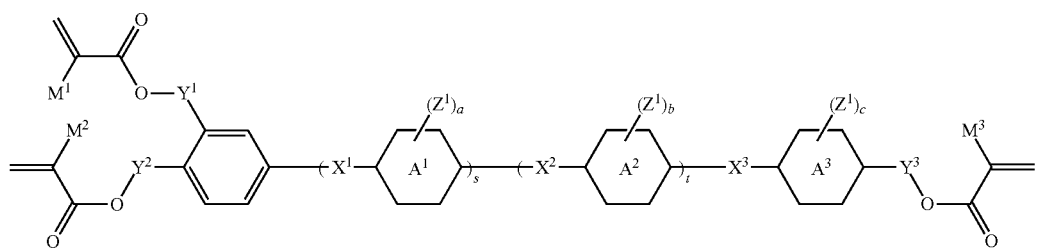

wherein $M^1$, $M^2$, and $M^3$ each independently represent a hydrogen atom, a methyl group, or a halogen atom; ring $A^1$, ring $A^2$, and ring $A^3$ each independently represent a benzene ring, a cyclohexane ring, a cyclohexene ring, a naphthalene ring, a decahydronaphthalene ring, a tetrahydronaphthalene ring, or a phenanthrene ring, the —CH= moiety of each of which rings is optionally displaced with —N= or the —CH$_2$— moiety of each of which rings is optionally displaced with —S— or —O—; at least one of ring A$^1$, ring A$^2$, and ring A$^3$ is a naphthalene ring; Z$^1$, Z$^2$, and Z$^3$ each independently represent an alkyl group having 1 to 6 carbon atoms, optionally substituted with a halogen atom or a cyano group, and optionally having a methylene group thereof interrupted by —O— or —CO—; X$^1$, X$^2$, and X$^3$ each independently represent a single bond, —COO—, —OCO—, —(CH$_2$)$_p$—, —CH=CH—, —(CH$_2$)$_p$O—, —O(CH$_2$)$_p$—, —CH=CHCH$_2$O—, —OCH$_2$CH=CH—, —C≡C—, —(CH$_2$)$_p$COO—, —OCO(CH$_2$)$_p$—, —(CH$_2$)$_p$OCO—O—, —OCO—O(CH$_2$)$_p$—, —(CH$_2$)$_q$O(CH$_2$)$_r$O—, or —O(CH$_2$)$_q$O(CH$_2$)$_p$—; Y$^1$ and Y$^2$ each independently represent -L$^1$-, -L$^1$O—, -L$^1$O—CO—, -L$^1$CO—O—, or -L$^1$O—CO—O—; Y$^3$ represents a single bond, -L$^2$-, —OL$^2$-, —O—COL$^2$-, —CO—OL$^2$-, or —O—CO—OL$^2$-; L$^1$ and L$^2$ each independently represent an alkylene group having 1 to 8 carbon atoms optionally interrupted by one to three —O— linkages; a, b, and c represent the numbers of the substituents on ring A$^1$, ring A$^2$, and ring A$^3$, respectively, each independently being an integer of (2u+2) or smaller, wherein u is the number of the 6-membered rings composing the substituted monocyclic or fused ring; at least one of a, b, and c is an integer of 1 or greater; p represents an integer of 1 to 8; q and r each independently represent an integer of 1 to 3; and s and t each independently represent 0 or 1, provided that s+t≧1.

The invention also provides a polymerizable composition containing the trifunctional (meth)acrylate compound, an optically anisotropic element obtained by photopolymerizing the polymerizable composition, and an optical film including the optically anisotropic element for use in a display device.

BEST MODE FOR CARRYING OUT THE INVENTION

Figure 1:
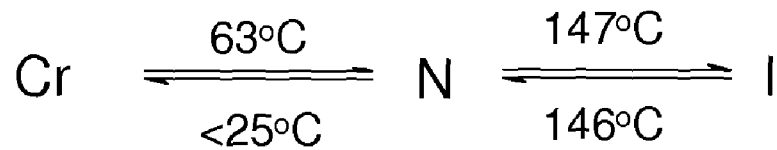
FIG. 1 schematically illustrates the thermal transition behavior of compound No. 1 prepared in Example 1-1.

The invention will be described in detail based on its preferred embodiments.

The trifunctional (meth)acrylate compound of the invention represented by general formula (I) will be described first.

In formula (I), the halogen atom as represented by M$^1$, M$^2$, M$^3$, Z$^1$, Z$^2$, or Z$^3$ or the halogen atom that may substitute the alkyl group having 1 to 6 carbon atoms as represented by Z$^1$, Z$^2$, or Z$^3$ is exemplified by fluorine, chloride, bromine, and iodine.

Examples of the alkyl group having 1 to 6 carbon atoms as represented by Z$^1$, Z$^2$, or Z$^3$ in formula (I) include methyl, ethyl, propyl, isopropyl, butyl, sec-butyl, tert-butyl, isobutyl, amyl, isoamyl, tert-amyl, hexyl, 2-hexyl, and 3-hexyl. The alkyl group is optionally substituted with a halogen atom or a cyano group, and the methylene group of the alkyl group is optionally interrupted by —O— or —CO—.

Examples of the alkylene group having 1 to 8 carbon atoms as represented by L$^1$ or L$^2$ in formula (I) include methylene, ethylene, propylene, trimethylene, tetramethylene, butane-1,3-diyl, 2-methylpropane-1,3-diyl, 2-methylbutane-1,3-diyl, pentane-2,4-diyl, pentane-1,4-diyl, 3-methylbutane-1,4-diyl, 2-methylpentane-1,4-diyl, pentamethylene, hexamethylene, heptamethylene, and octamethylene. These alkylene groups may be interrupted by one to three —O— linkages.

Of the trifunctional (meth)acrylate compounds of formula (I) those in which each of ring A$^1$, ring A$^2$, and ring A$^3$ is a benzene ring or a naphthalene ring, and at least one of them is a naphthalene ring are preferred because of their broad liquid crystal temperature ranges and low crystallizing properties that favor liquid crystal phase stability in low temperatures, and those in which X$^1$, X$^2$, and X$^3$ are each —COO— or —COO— are preferred because of improved liquid crystal alignment properties. More preferred are those in which ring A$^3$ is a naphthalene ring because of their still lower crystallizing properties. Even more preferred are those which are alone capable of maintaining a liquid crystal phase at or below 30° C. because they exhibit a liquid crystal phase in a practical working temperature range (i.e., room temperature).

Specific examples of the trifunctional (meth)acrylate compound of general formula (I) include, but are not limited to, the compounds of [Formula 2] to [Formula 4] below.

[Formula 2]

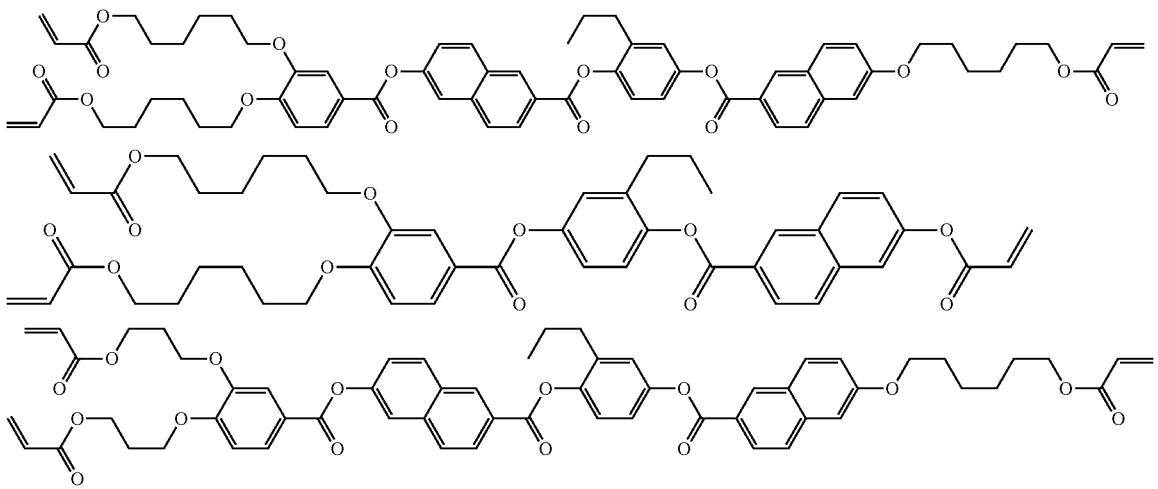

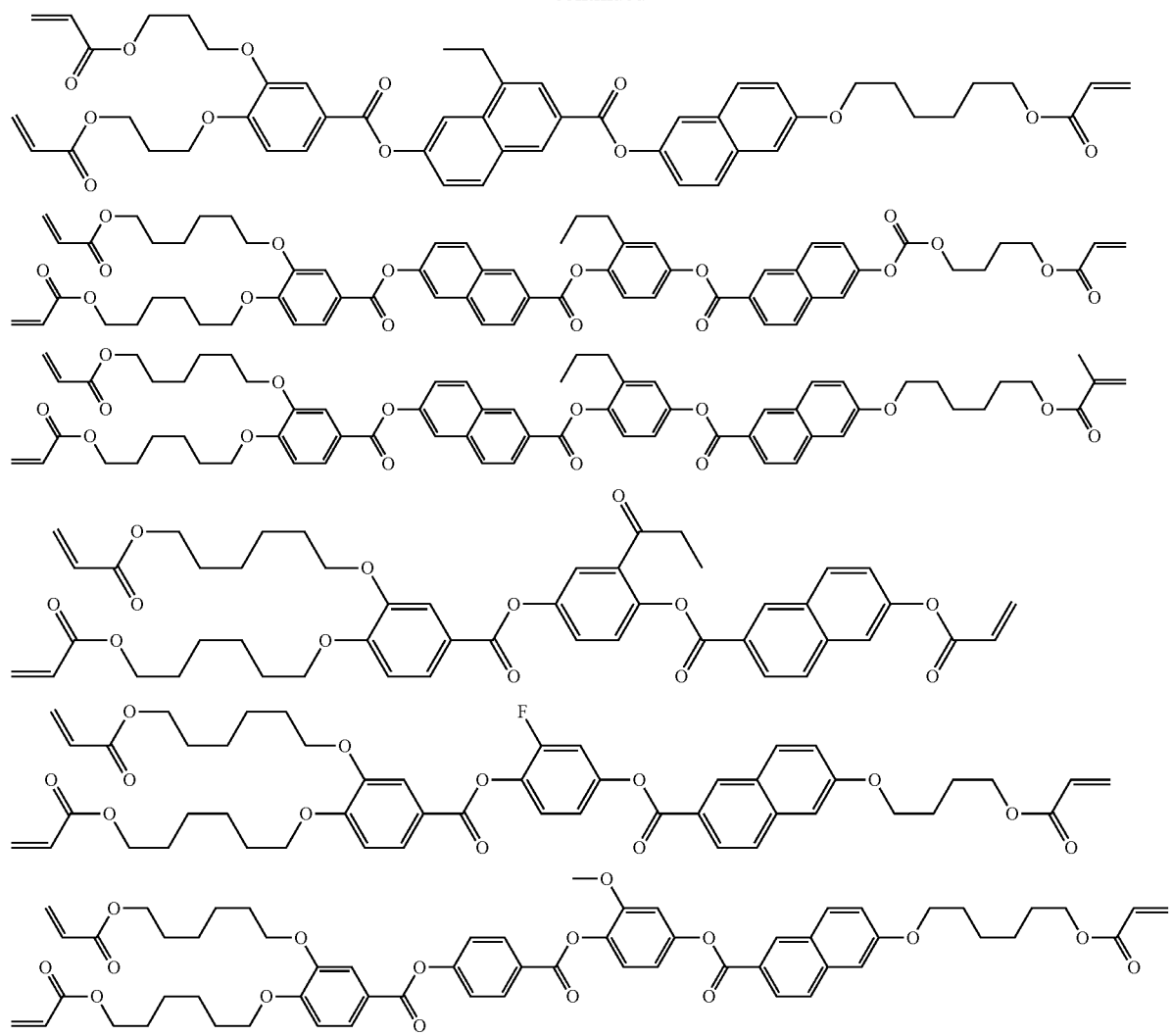
[Formula 3]
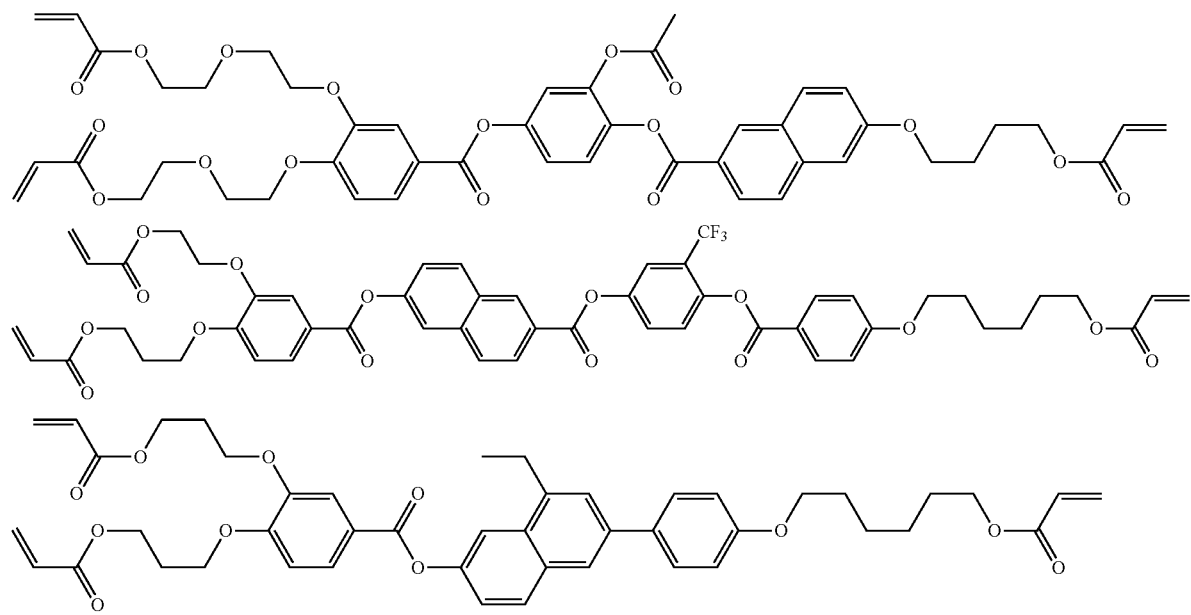

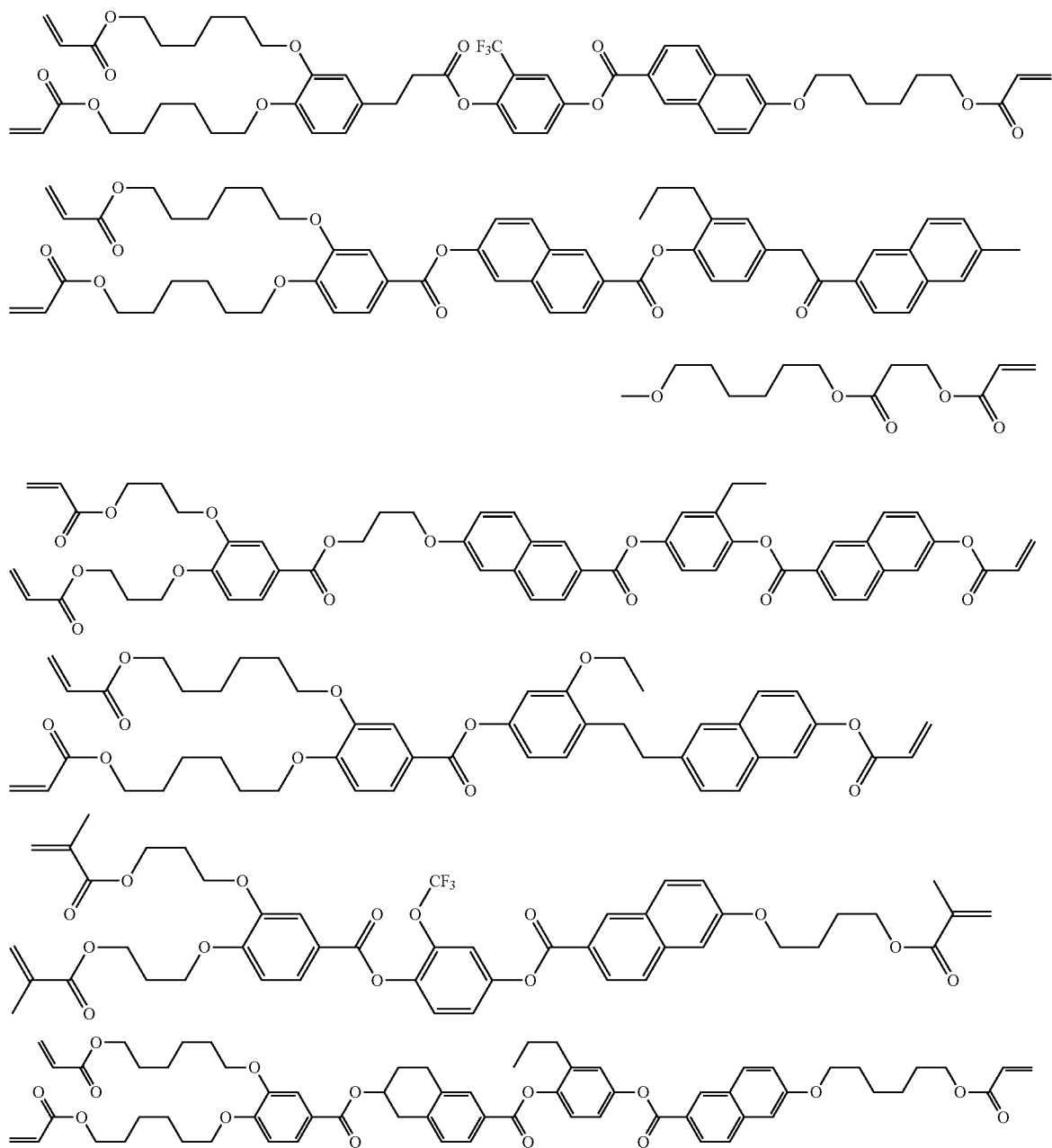
[Formula 4]
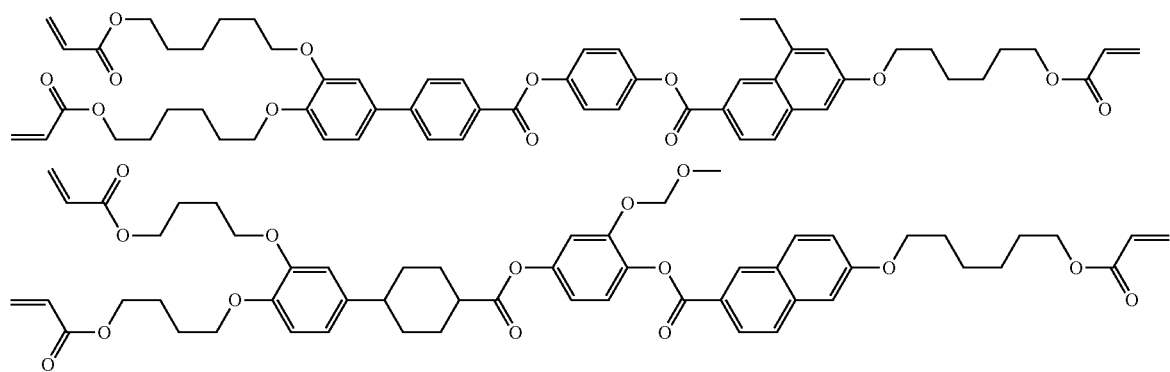

-continued

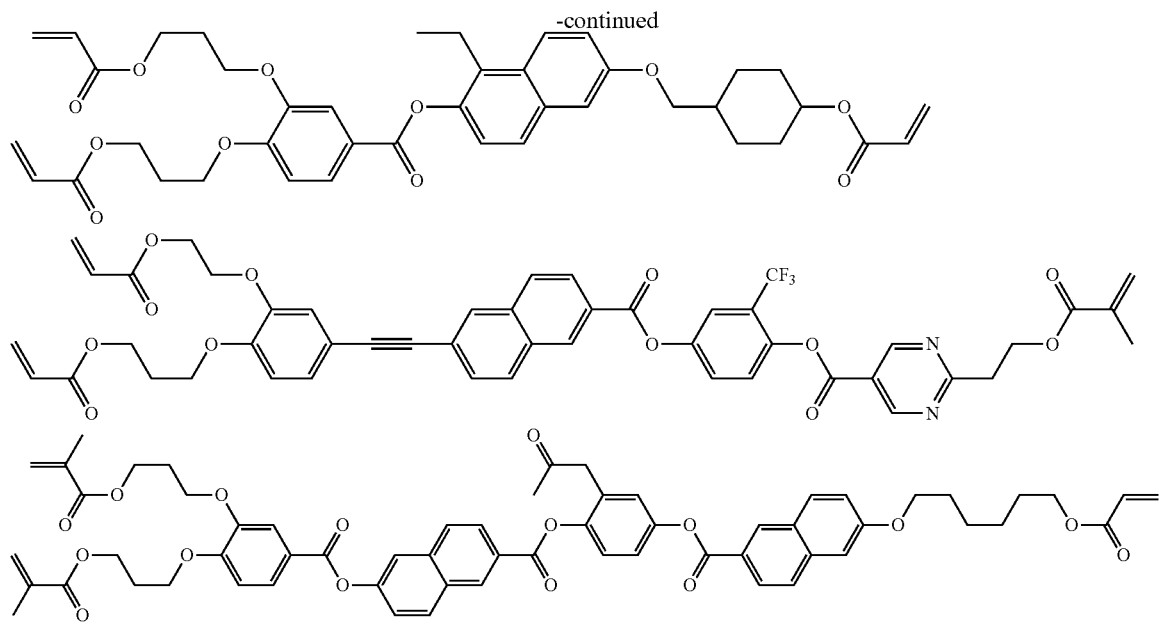

The trifunctional (meth)acrylate compound of the invention is not limited by the process of preparation and may be prepared using any known reactions, for example, as follows. The hydroxyl group of a phenol or naphthol compound (including a hydroxyl group bonded via $Y^1$, $Y^2$, or $Y^3$) is esterified with a (meth)acrylic halide to form a (meth)acryloyloxy intermediate. Two molecules of the (meth)acryloyloxy intermediate are caused to react with each other to form $X^1$, $X^2$, or $X^3$ according to reaction scheme of [Formula 5] below to produce a trifunctional (meth)acrylate compound of the invention.

The trifunctional (meth)acrylate compound of the invention obtained by the reaction scheme of [Formula 5] below is a compound in which $X^1$, $X^2$, or $X^3$ is —COO— or —COO—, and the (meth)acryloyloxy group is included in the $R^1$ moiety and the $R^2$ moiety.

[Formula 5]

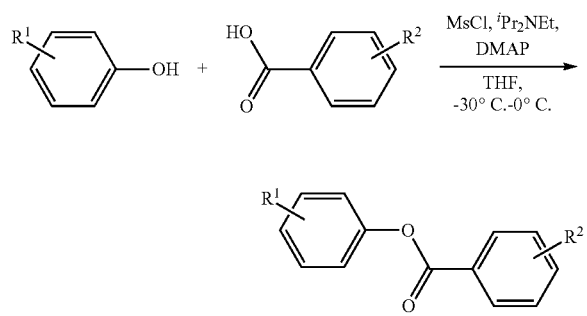

MsCl: Methanesulfonyl chloride
$^iPr_2NEt$: Diisopropylethylamine
DMAP: 4-dimethylaminopyridine
THF: Tetrahydrofuran The trifunctional (meth)acrylate compound of the invention as compounded, if necessary, with a liquid crystal material is preferably used as a material for making an optically anisotropic element excellent in hardness, heat resistance, liquid crystal alignment fixing ability, optical characteristics, and solvent resistance. It is also useful as a monomer for polymer dispersed liquid crystals (PDLC) and a material for making a liquid crystal alignment film, a liquid crystal alignment controlling film, a coating material, a protective film, and so on.

The polymerizable composition of the invention will then be described.

The polymerizable composition of the invention contains the trifunctional (meth)acrylate compound of the invention and is preferably used as a material for making an optically anisotropic element. The polymerizable composition of the invention may contain a liquid crystal compound in addition to the trifunctional (meth)acrylate compound. As used herein, the term "liquid crystal compound" is intended to include a known liquid crystal compound, a known liquid crystal-like compound, and a mixture thereof.

Taking the sum of the trifunctional (meth)acrylate compound and the liquid crystal compound as 100 parts by mass, the content of the trifunctional (meth)acrylate compound in the polymerizable composition is preferably 3 to 100 parts, more preferably 5 to 100 parts, by mass. Less than 3 parts by mass of the trifunctional (meth)acrylate compound can fail to produce the intended effects.

When a polymer with increased hardness is desired, it is preferred to increase the ratio of the trifunctional (meth)acrylate compound, specifically to 70 to 100 parts by mass. When a polymer with enhanced alignment uniformity is desired, the trifunctional (meth)acrylate compound is preferably compounded with the liquid crystal compound so that the ratio of the trifunctional (meth)acrylate compound may range from 30 to 70 parts by mass.

The liquid crystal compound to be compounded into the polymerizable composition is usually chosen from those commonly used. Examples of the liquid crystal compounds include, but are not limited to, the compounds of [Formula 6] and [Formula 7] below.

[Formula 6]
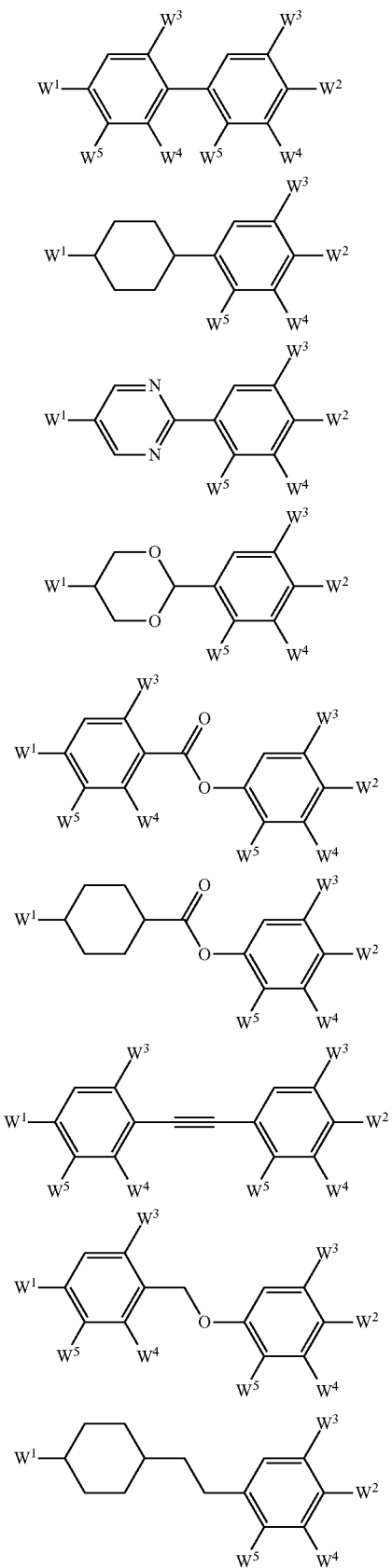
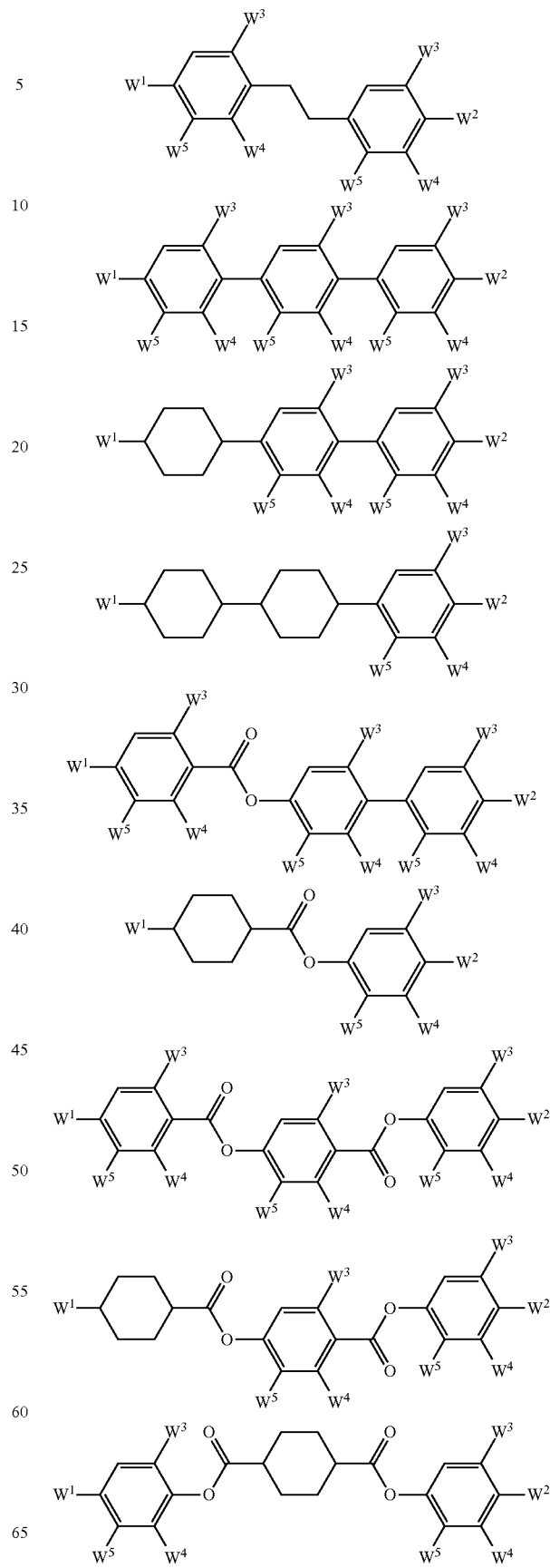

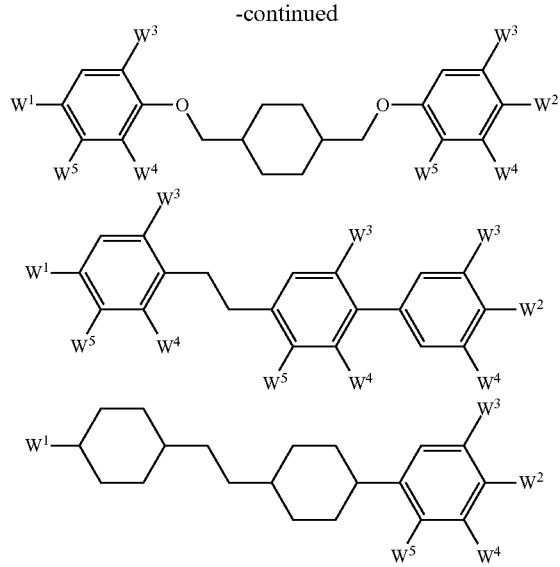

[Formula 7]

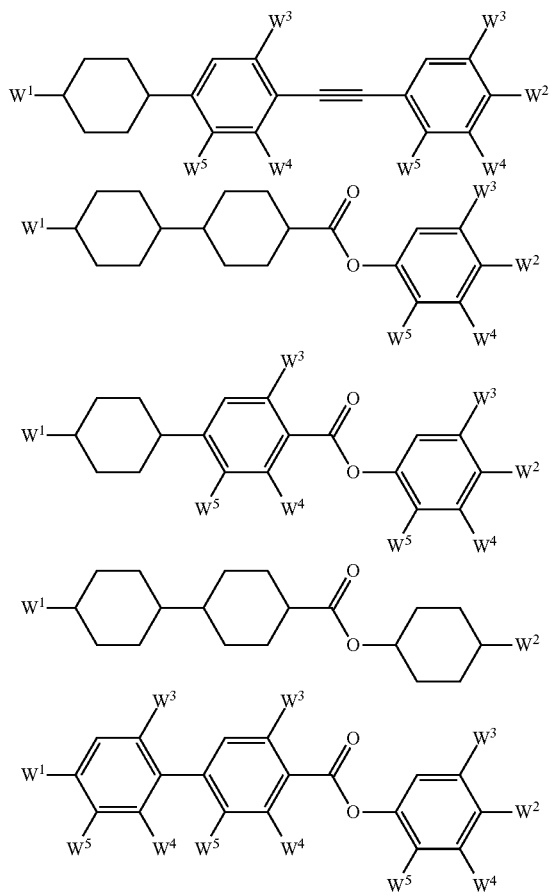

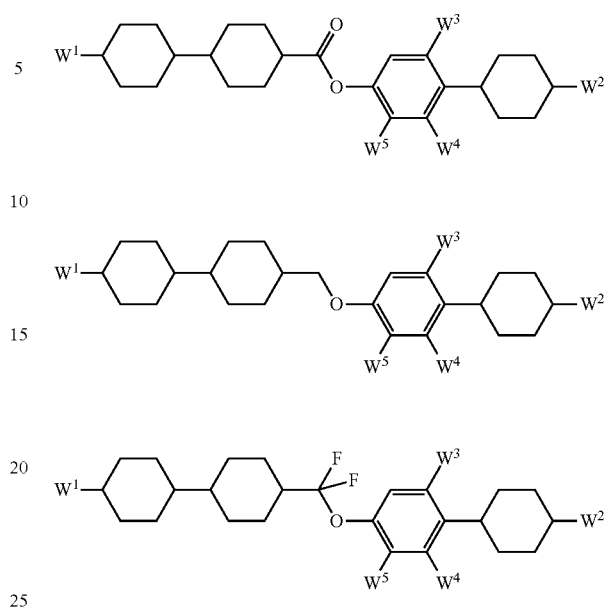

wherein $W^1$ represents a hydrogen atom, an optionally branched alkyl group having 1 to 8 carbon atoms, an optionally branched alkoxy group having 1 to 8 carbon atoms, an optionally branched alkenyl group having 1 to 8 carbon atoms, an optionally branched alkenyloxy group having 1 to 8 carbon atoms, an optionally branched alkynyl group having 1 to 8 carbon atoms, an optionally branched having 1 to 8 carbon atoms, alkynyloxy group, an optionally branched alkoxyalkyl group having 1 to 8 carbon atoms, an optionally branched alkanoyloxy group having 1 to 8 carbon atoms, or an optionally branched alkoxycarbonyl group having 1 to 8 carbon atoms, each of which may be substituted with, e.g., a halogen atom or a cyano group; $W^2$ represents a cyano group, a halogen atom, or a group represented by $W^1$; and $W^3$, $W^4$, and $W^5$ each represent a hydrogen atom, a halogen atom, or a cyano group.

It is preferred that the liquid crystal compound to be used in the polymerizable composition have a polymerizable functional group. Preferred examples of the polymerizable functional group include a (meth)acryloyloxy group, a fluoroacrylic group, a chloroacrylic group, a trifluoromethylacrylic group, an oxirane ring (epoxy group), an oxetane ring, a styrene compound (styryl group), a vinyl group, a vinyl ether group, a vinyl ketone group, a maleimide group, or a phenylmaleimide group. Any commonly used liquid crystal compounds having such polymerizable functional group are useful. Examples of such compounds include, but are not limited to, those described in JP 2005-15473A, paras. [0172] through [0314] and compounds of [Formula 8] to [Formula 18] below.

[Formula 8]

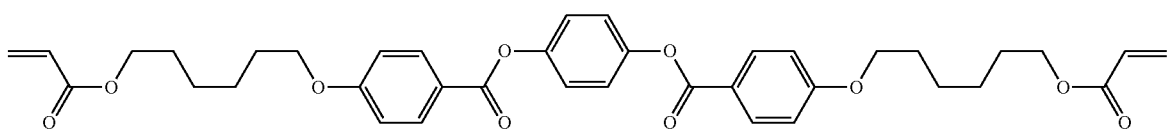

-continued
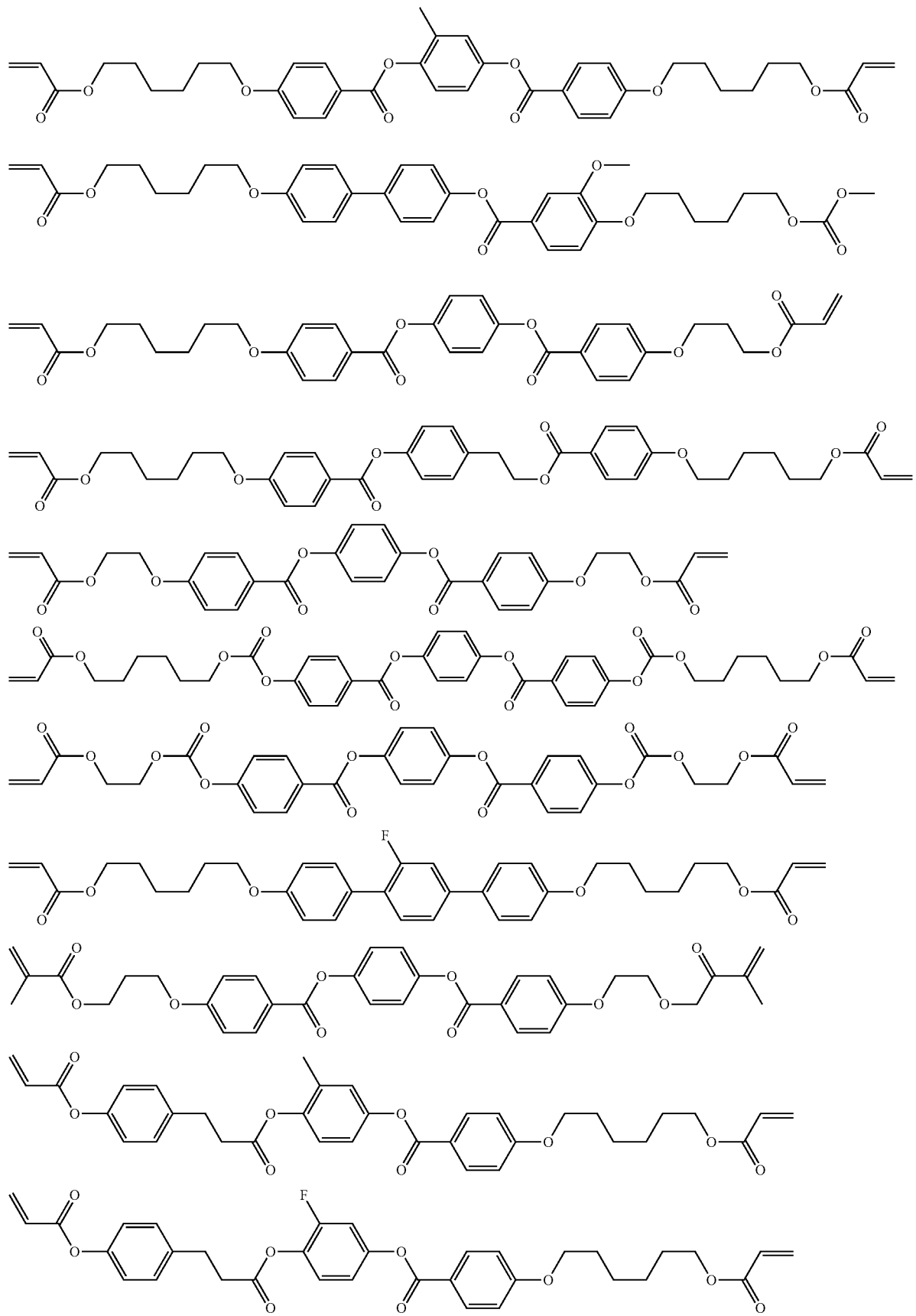

[Formula 9]
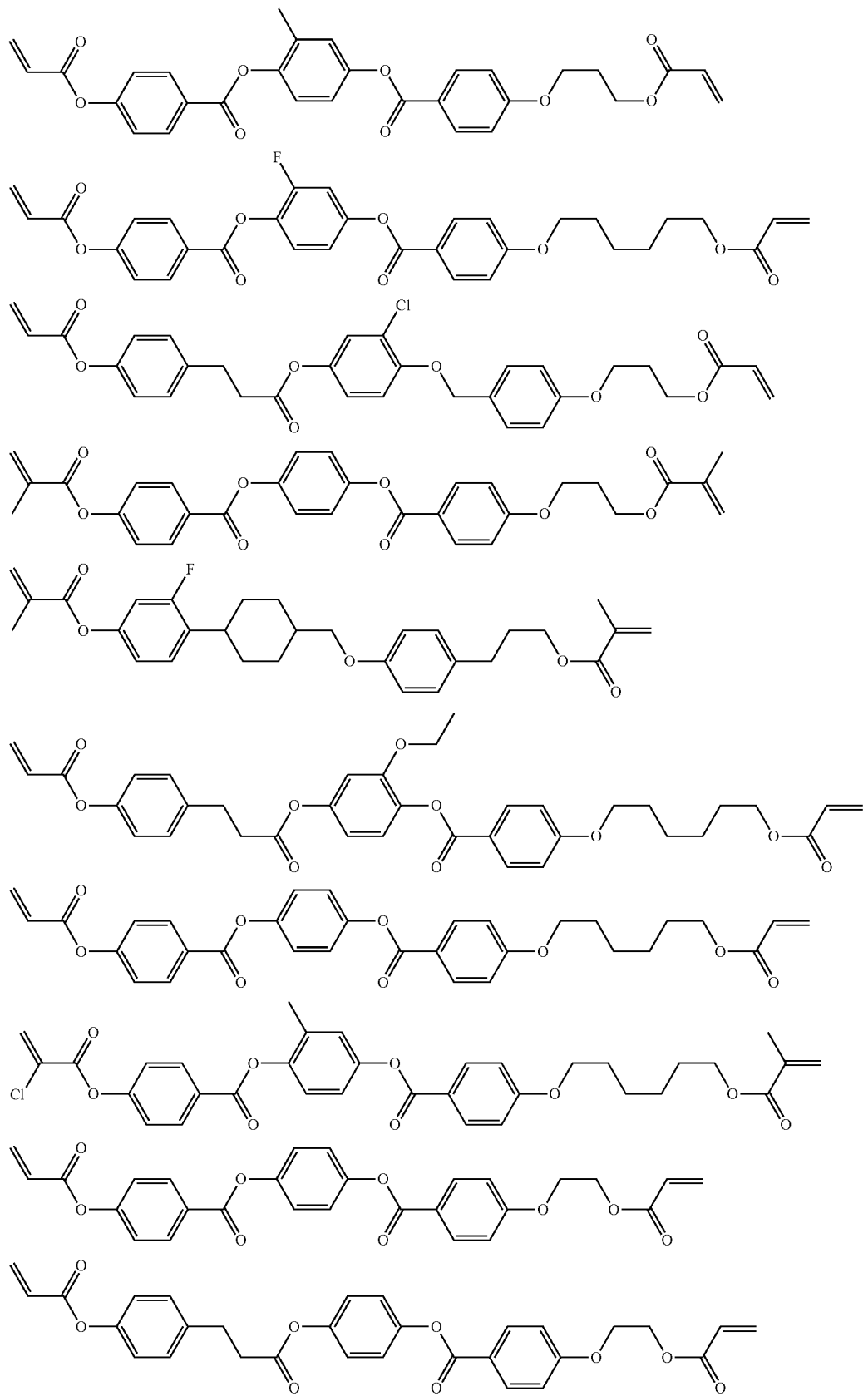

[Formula 10]
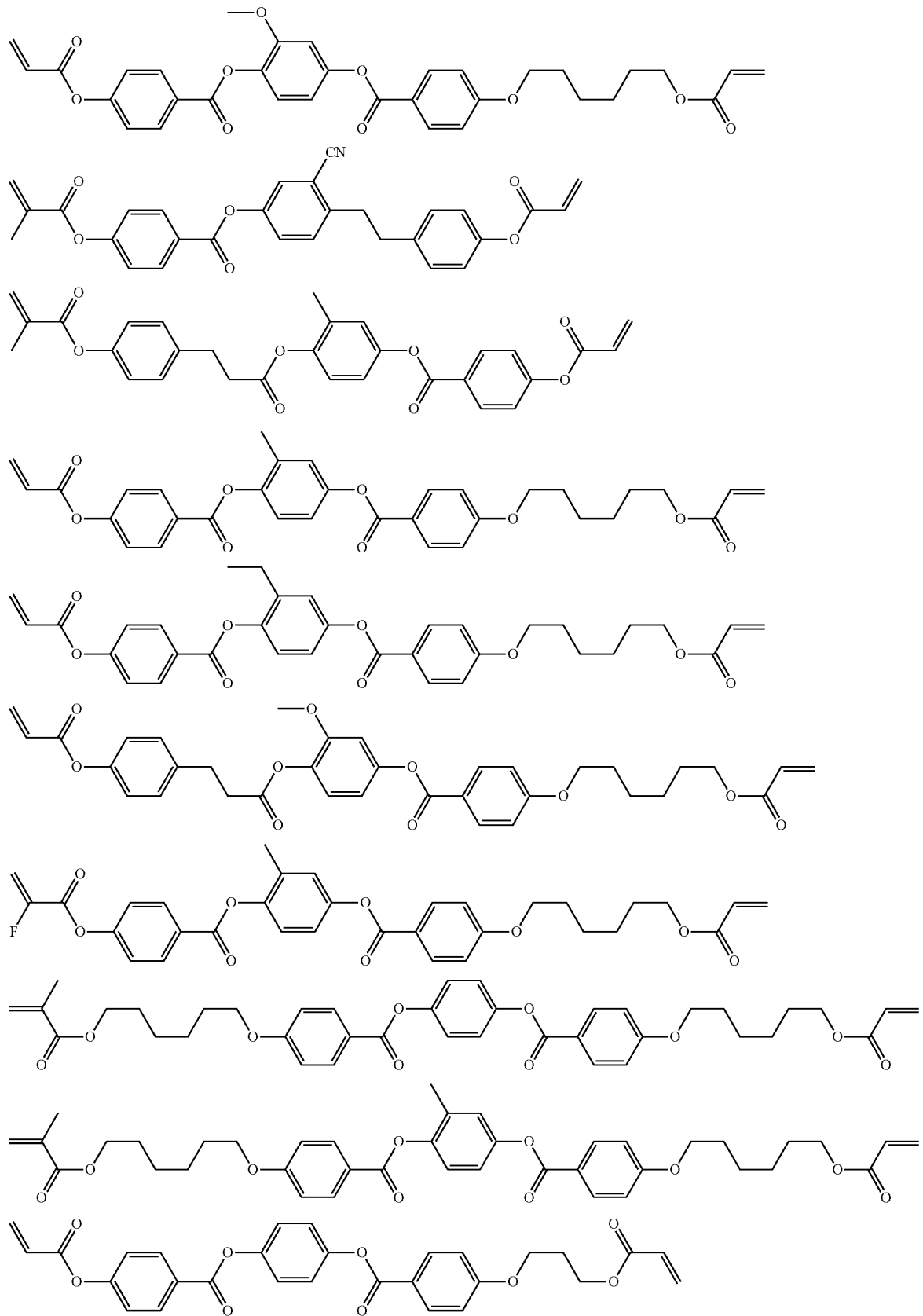

-continued
[Formula 11]
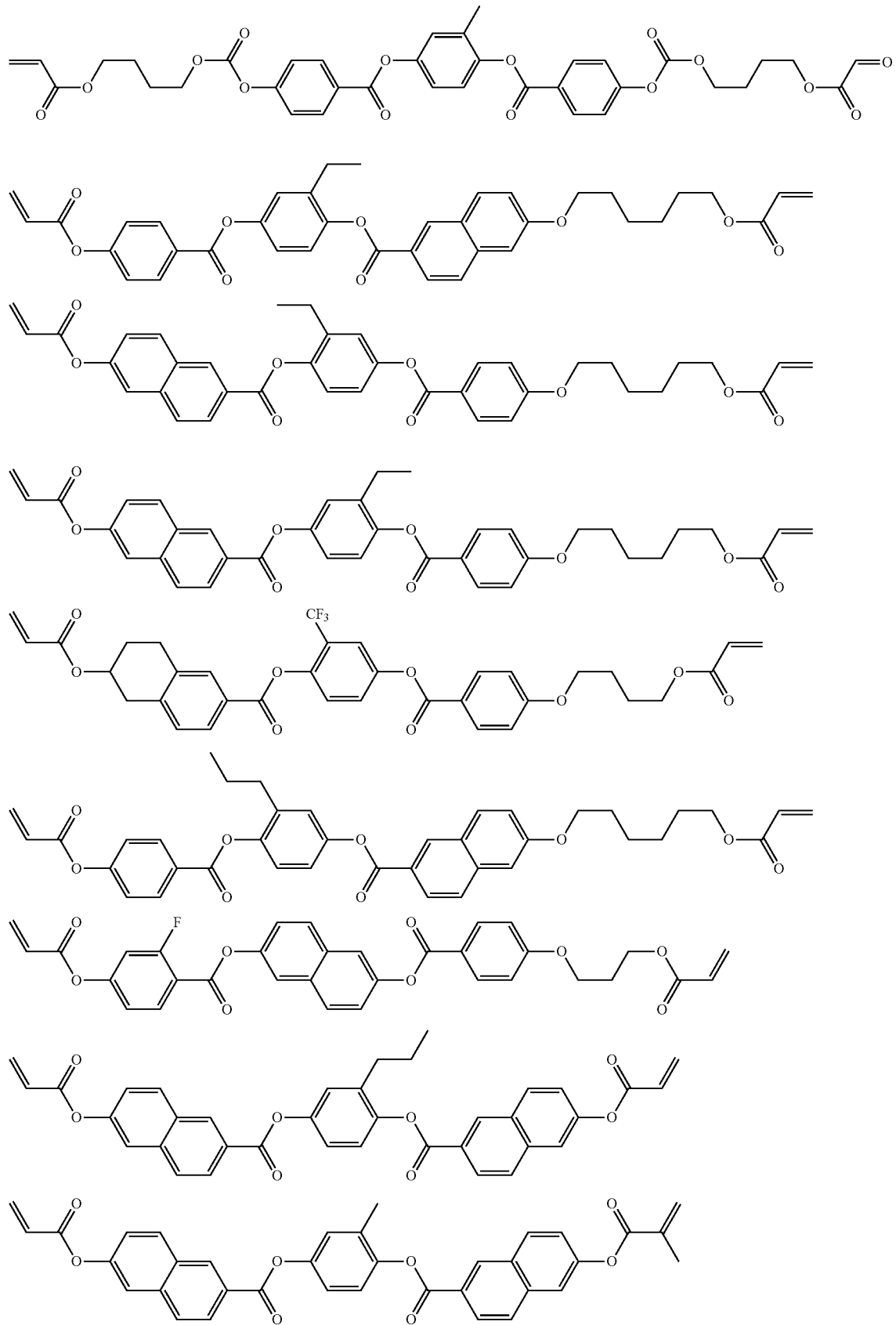

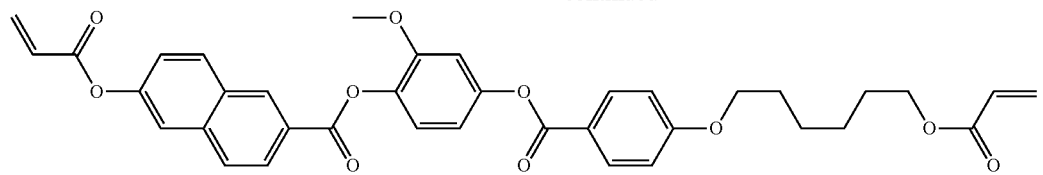
[Formula 12]
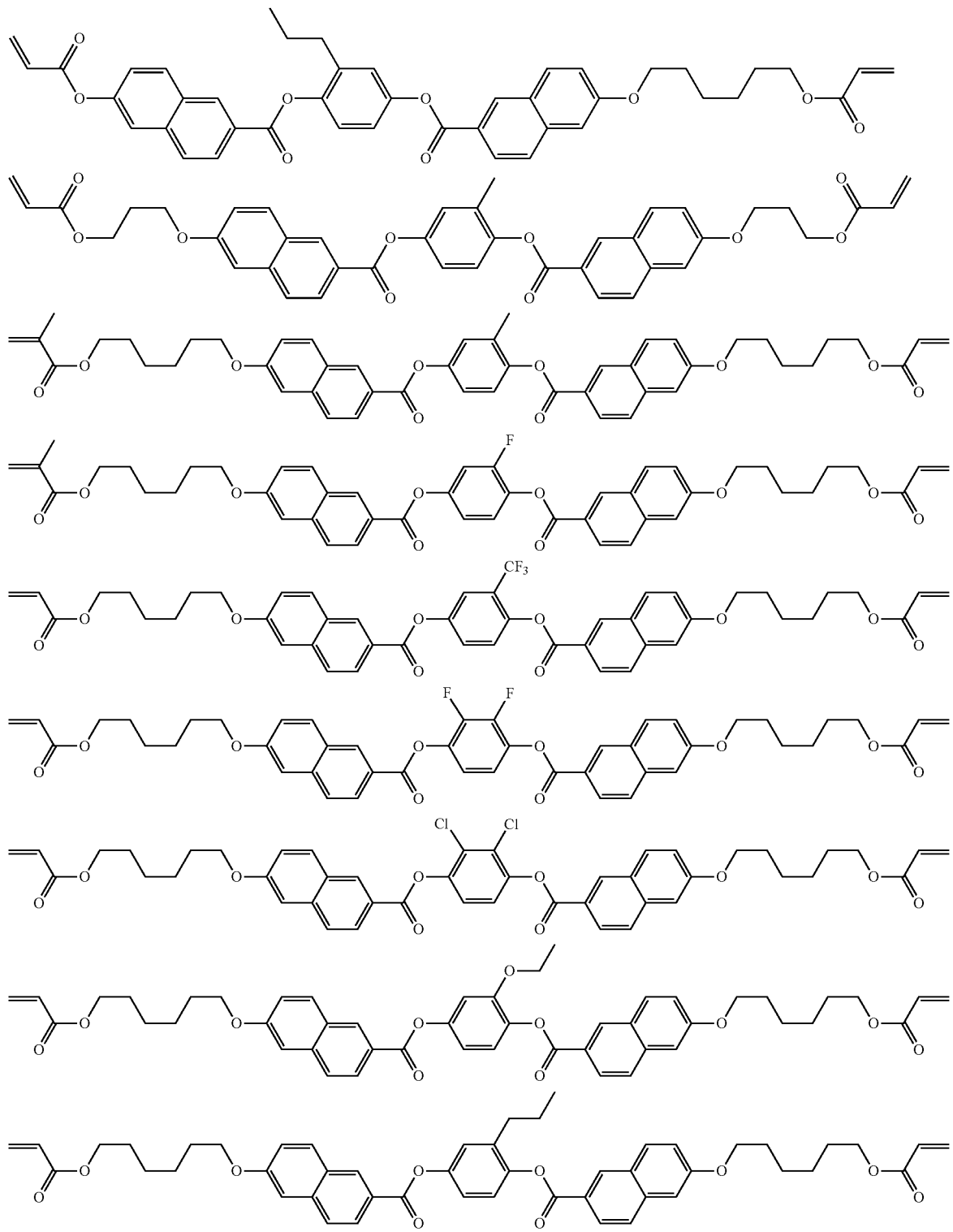

[Formula 13]
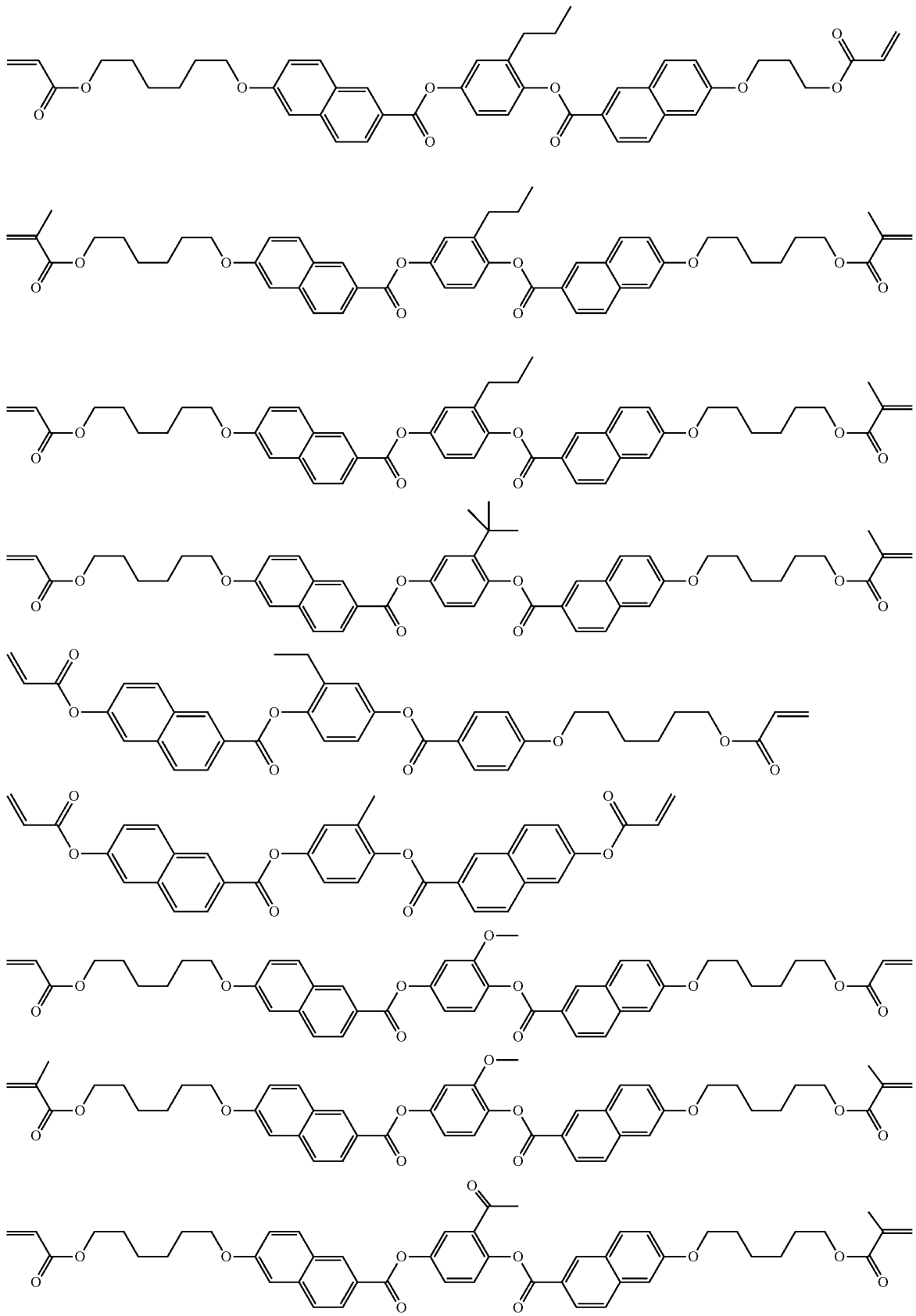

[Formula 14]
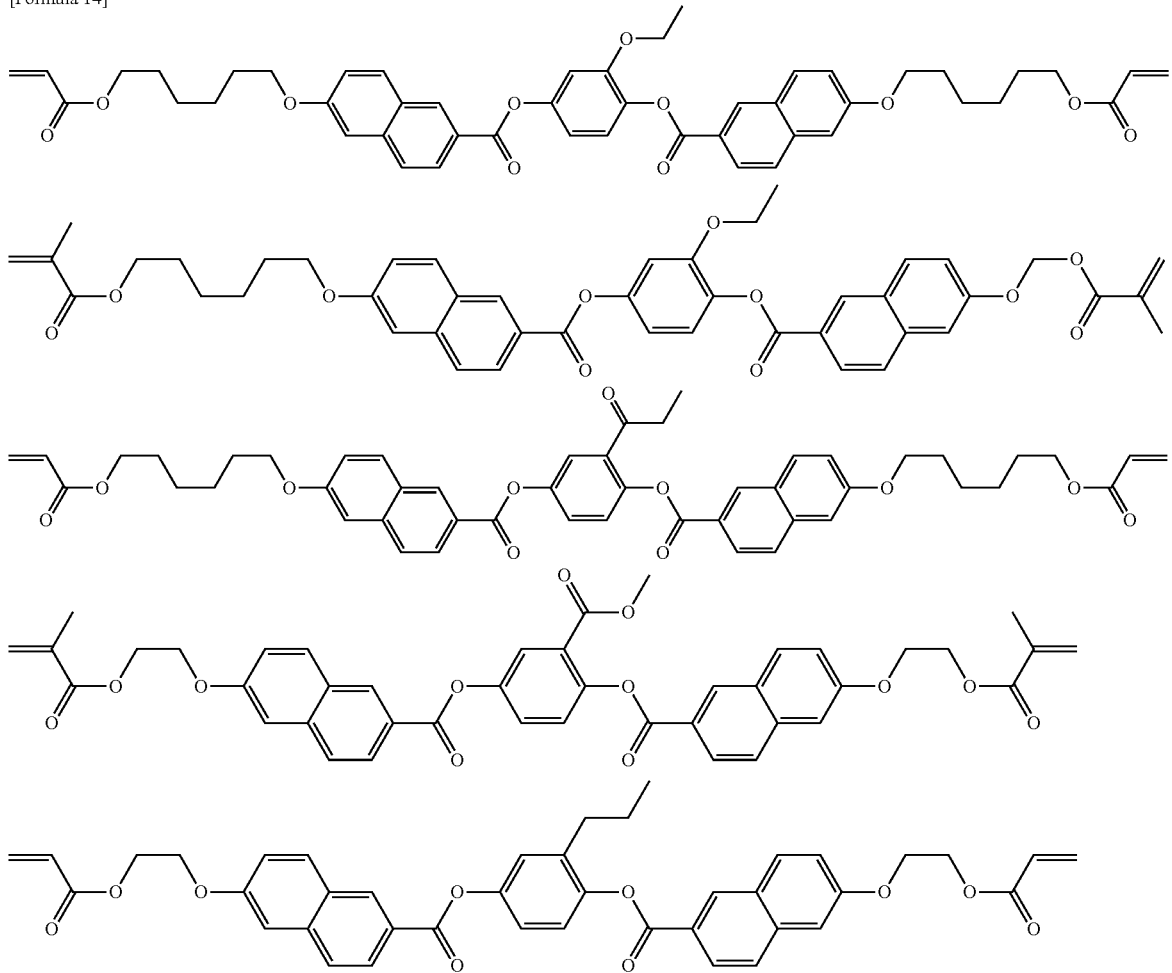
[Formula 15]
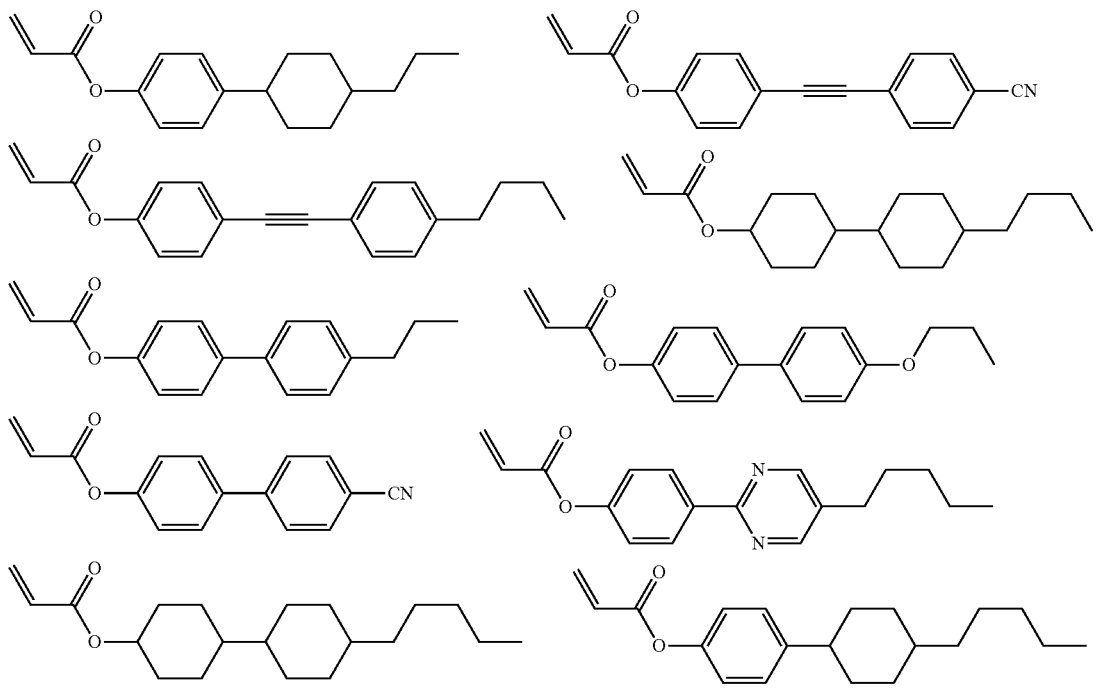

-continued
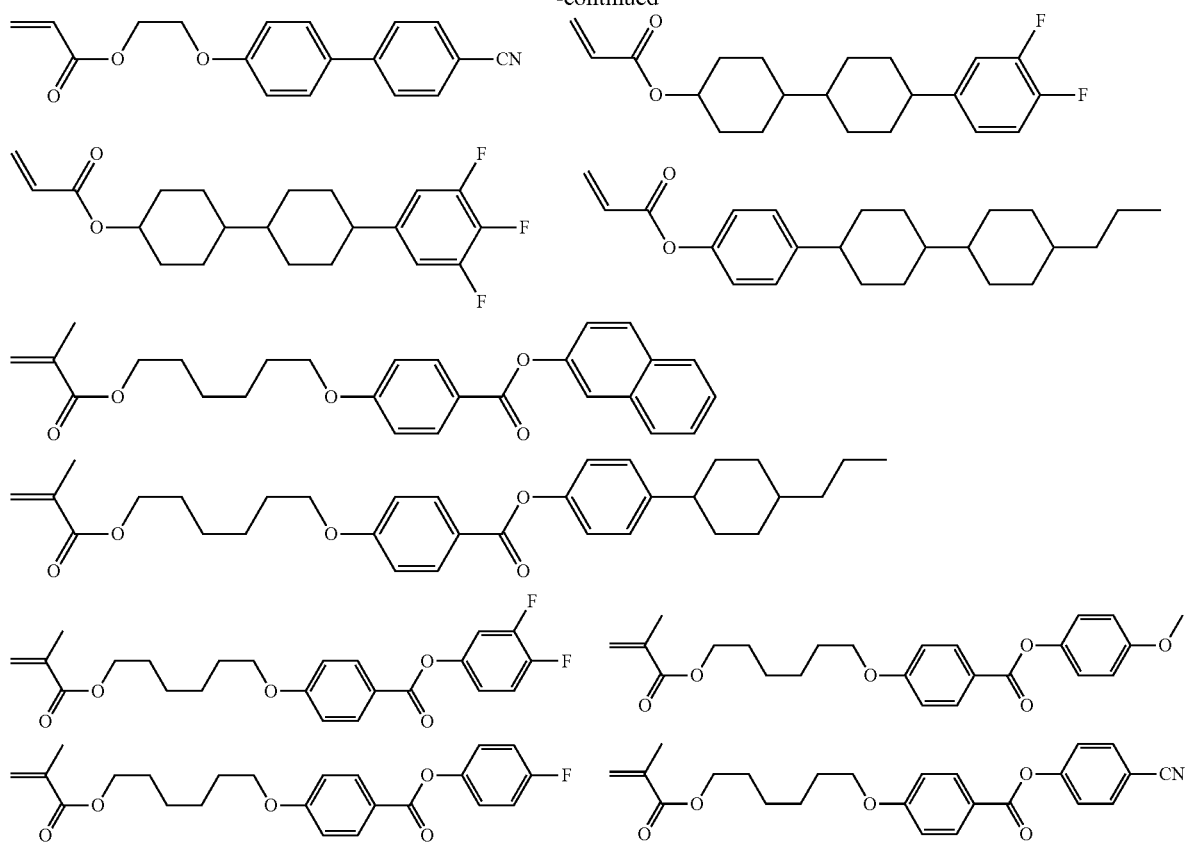
[Formula 16]
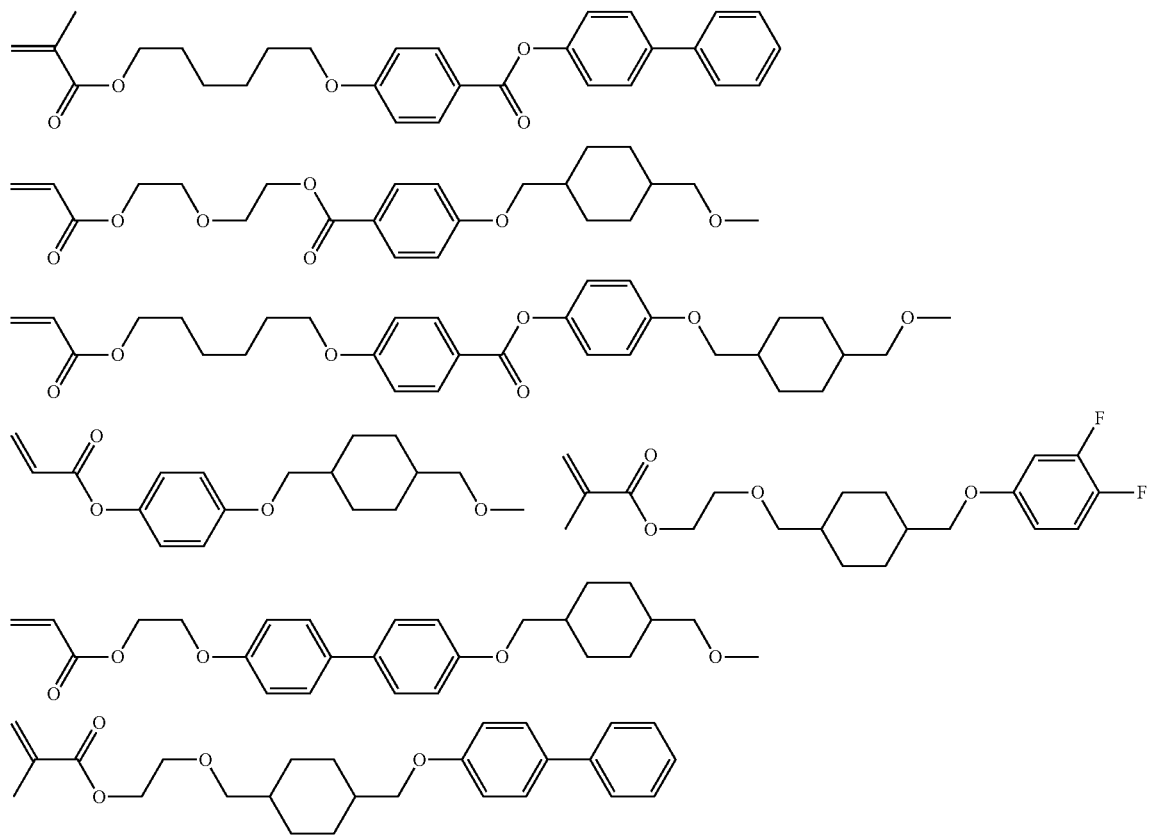

-continued
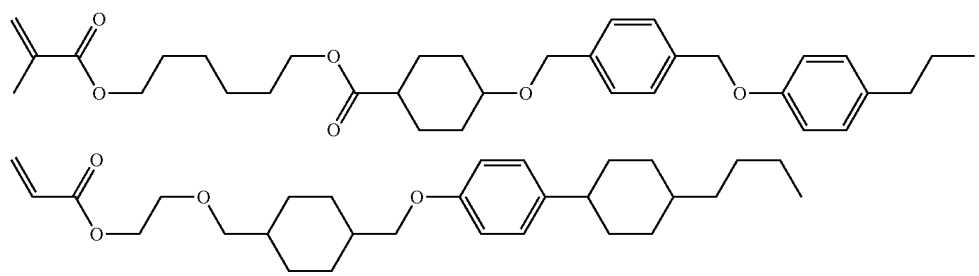
[Formula 17]
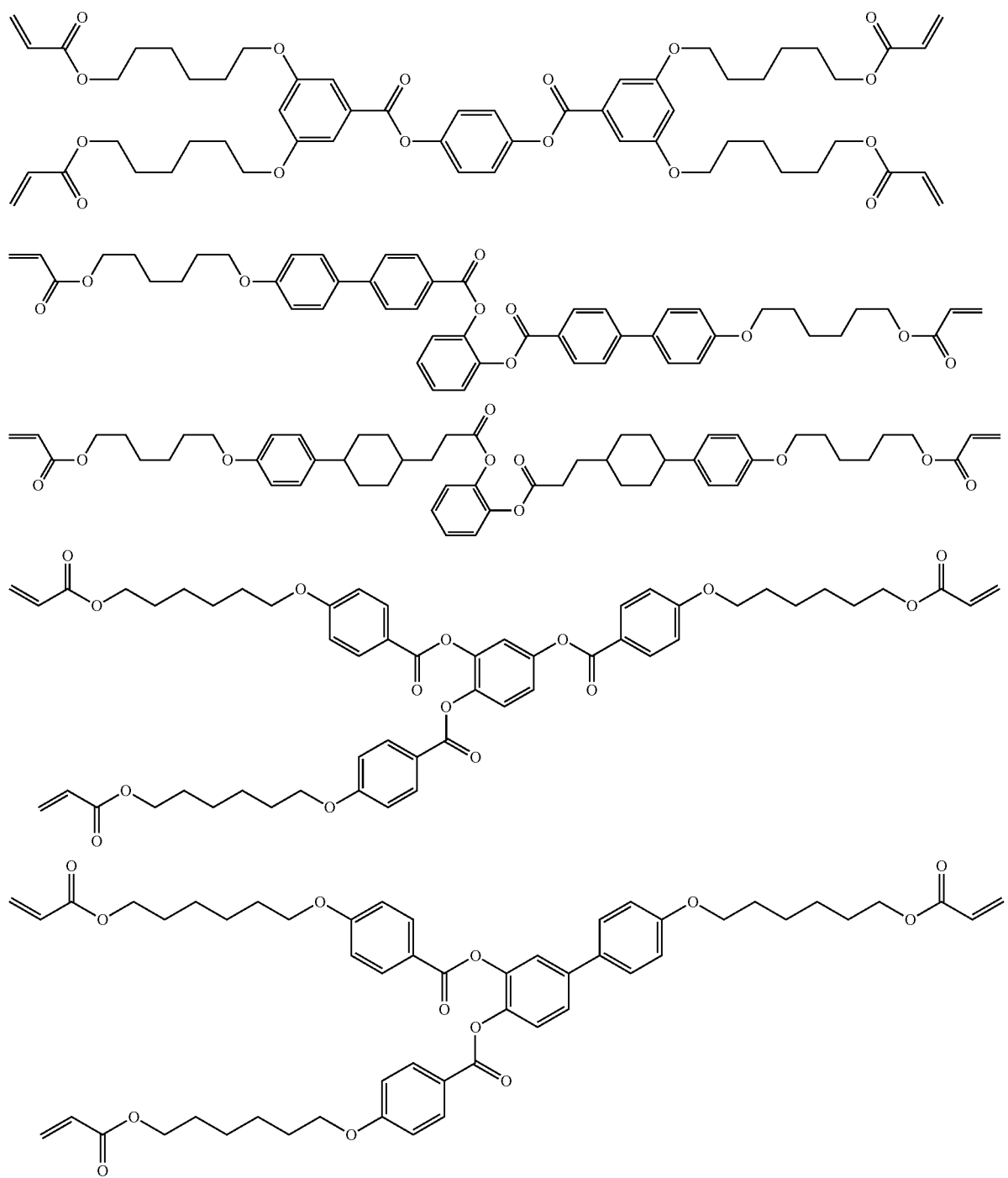

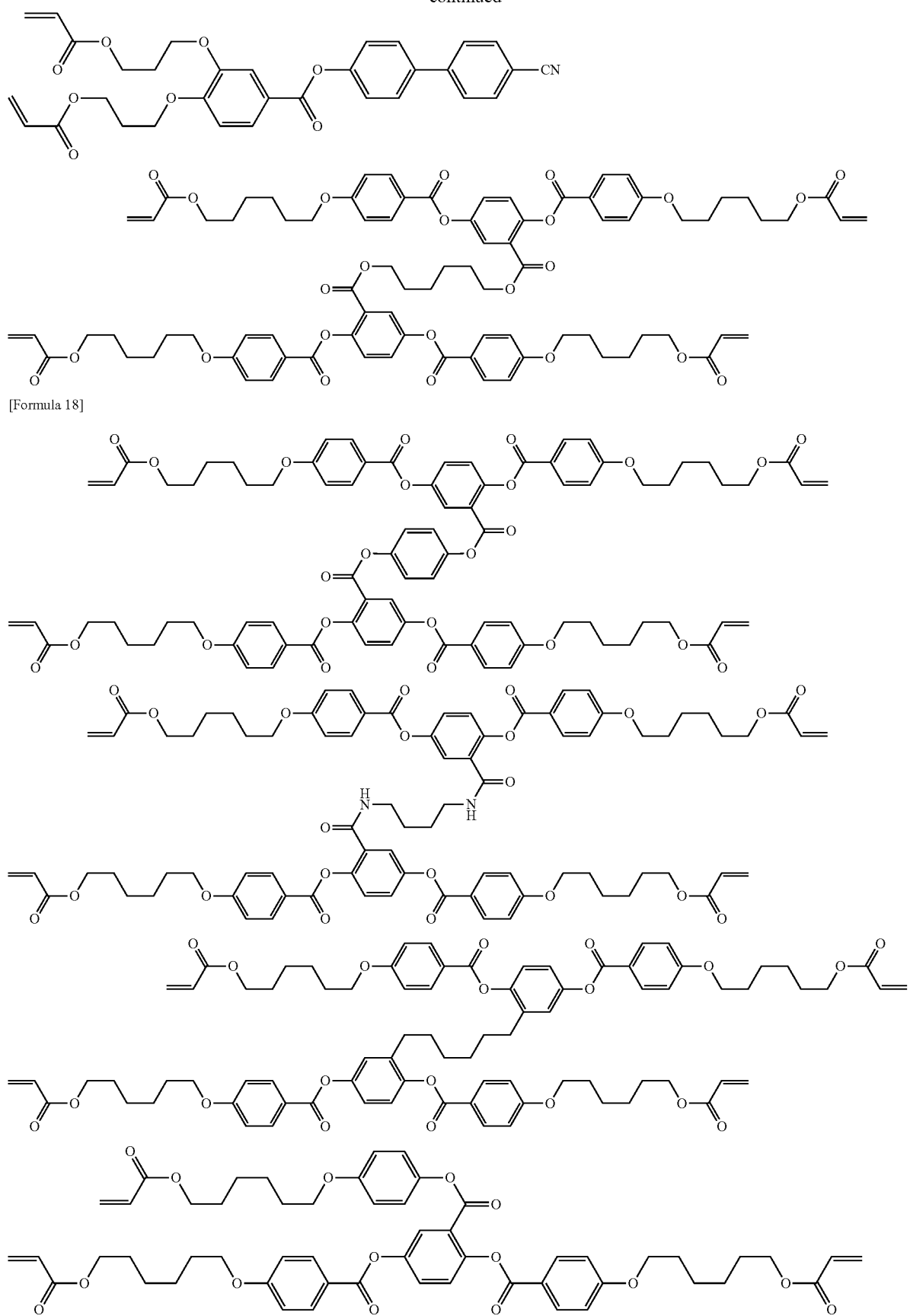
[Formula 18]

-continued

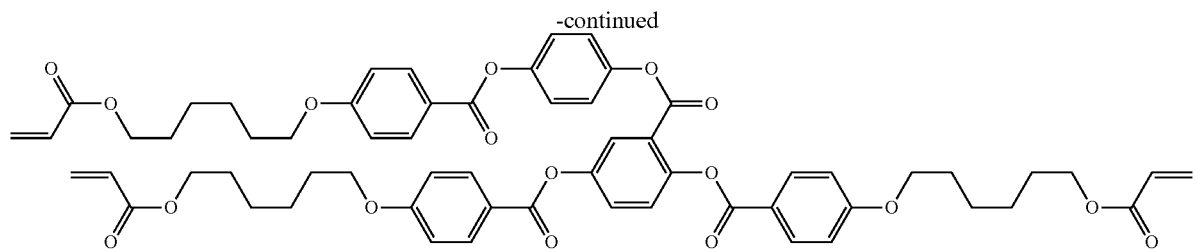

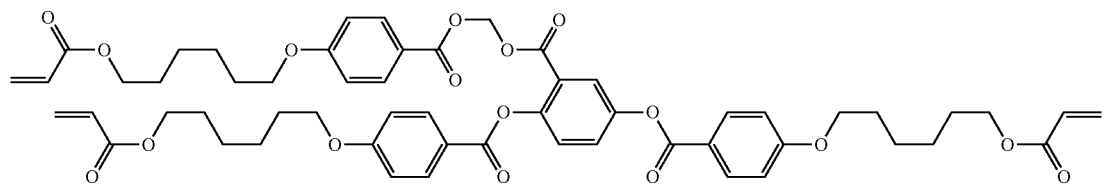

Where necessary, the polymerizable composition of the invention may contain other monomer (a compound having an ethylenically unsaturated bond) and a radical polymerization initiator and be formulated into a solution in a solvent.

Examples of the other monomers include (meth)acrylic esters, such as methyl (meth)acrylate, ethyl (meth)acrylate, propyl (meth)acrylate, butyl (meth)acrylate, sec-butyl (meth) acrylate, tert-butyl (meth)acrylate, hexyl (meth)acrylate, 2-ethylhexyl (meth)acrylate, tetrahydrofurfuryl (meth)acrylate, glycidyl (meth)acrylate, allyl (meth)acrylate, allyloxy (meth)acrylate, cyclohexyl (meth)acrylate, benzyl (meth) acrylate, 1-phenylethyl (meth)acrylate, 2-phenylethyl (meth) acrylate, furfuryl (meth)acrylate, diphenylmethyl (meth) acrylate, naphthyl (meth)acrylate, pentachlorophenyl (meth) acrylate, 2-chloroethyl (meth)acrylate, methyl α-chloro (meth)acrylate, phenyl α-bromo(meth)acrylate, trifluoroethyl (meth)acrylate, tetrafluoropropyl (meth)acrylate, polyethylene glycol di(meth)acrylate, 1,4-butanediol di(meth)acrylate, 1,6-hexanediol di(meth)acrylate, trimethylolpropane tri(meth)acrylate, pentaerythritol tri(meth)acrylate, pentaerythritol tetra(meth)acrylate, dipentaerythritol penta(meth)acrylate, and dipentaerythritol hexa(meth)acrylate; diacetoneacrylamide, styrene, vinyltoluene, and divinylbenzene.

The monomers described above may be used in any ratio that does not impair the expected effects of the polymerizable composition of the invention in terms of hardness, heat resistance, solvent resistance, and optical characteristics of resulting polymers. In order to secure these effects, the content of the other monomer is preferably not more than 50 parts by mass, more preferably 30 parts by mass or less, per 100 parts by mass of the sum of the trifunctional (meth)acrylate compound and the liquid crystal compound.

Known radical polymerization initiators may be used in the polymerizable composition. Examples thereof include benzoyl peroxide, 2,2'-azobisisobutyronitrile, benzophenone, phenyl biphenyl ketone, 1-hydroxy-1-benzoylcyclohexane, benzil, benzyl dimethyl ketal, 1-benzyl-1-dimethylamino-1-(4'-morpholinobenzoyl)propane, 2-morpholyl-2-(4'-methylmercapto)benzoylpropane, thioxanthone, 1-chloro-4-propoxythioxanthone, isopropylthioxanthone, diethylthioxanthone, ethylanthraquinone, 4-benzoyl-4'-methyldiphenyl sulfide, benzoin butyl ether, 2-hydroxy-2-benzoylpropane, 2-hydroxy-2-(4'-isopropyl)benzoylpropane, 4-butylbenzoyltrichloromethane, 4-phenoxybenzoyldichloromethane, methylbenzoyl formate, 1,7-bis(9'-acridinyl)heptane, 9-n-butyl-3,6-bis(2'-morpholinoisobutyroyl)carbazole, 2-methyl-1-[4-(methylthio)phenyl]-2-morpholinopropan-1-one, p-methoxyphenyl-2,4-bis(trichloromethyl)-s-triazine, 2-methyl-4,6-bis(trichloromethyl)-s-triazine, 2-phenyl-4,6-bis(trichloromethyl)-s-triazine, 2-naphthyl-4,6-bis(trichloromethyl)-s-triazine, 2-(p-butoxystyryl)-s-triazine, 2-(p-butoxystyryl)-5-trichloromethyl-1,3,4-oxadiazole, 9-phenylacridine, 9,10-dimethylbenzphenazine, benzophenone/Michler's ketone, hexaarylbiimidazole/mercaptobenzimidazole, thioxanthone/amine, bis(2,4,6-trimethylbenzoyl)-phenylphosphine oxide, and compounds described in JP 2000-80068A, JP 2001-233842A, JP 2005-97141A, JP 2006-516246A. Japanese patent Nos. 3860170 and 3798008, and WO2006/018973. Preferred compounds of them are compounds represented by general formula (A):

[Formula 19]

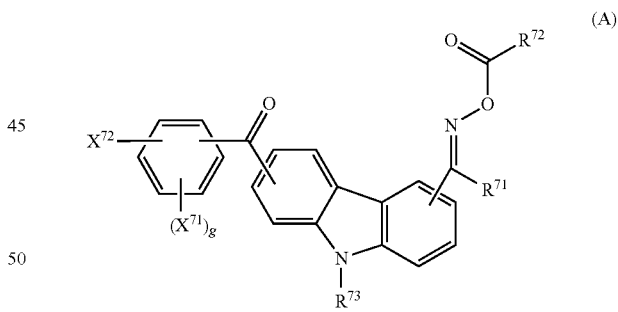

(A)

wherein $X^{71}$ represents a halogen atom or an alkyl group; $X^{72}$ represents a hydrogen atom, a halogen atom, an alkyl group, or a substituent represented by general formula (B) shown below; $R^{71}$, $R^{72}$, and $R^{73}$ each independently represent R, OR, COR, SR, CONRR', or CN, wherein R and R' each independently represent an alkyl group, an aryl group, an arylalkyl group, or a heterocyclic group, each of which may be substituted with a halogen atom and/or a heterocyclic group, and the alkylene moiety of the alkyl group and the arylalkyl group of which may be interrupted by an unsaturated bond, an ether bond, a thioether bond, or an ester bond, or R and R' may be taken together to form a ring; and g represents an integer of 0 to 4; and, when g is 2 or greater, two or more $X^{71}$'s may be the same or different.

[Formula 20]

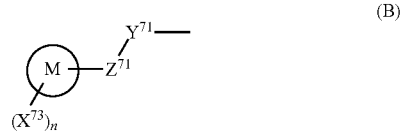

wherein ring M represents a cycloalkane ring, an aromatic ring, or a heterocyclic ring; $X^{73}$ represents a halogen atom or an alkyl group; $Y^{71}$ represents an oxygen atom, a sulfur atom, or a selenium atom; $Z^{71}$ represents an alkylene group having 1 to 5 carbon atoms; and h represents an integer of 0 to 4; when h is 2 or greater, two or more $X^{73}$'s may be the same or different.

A combination of the radical polymerization initiator and a sensitizer is also preferred. Examples of useful sensitizers are thioxanthone, phenothiazine, chlorothioxanthone, xanthone, anthracene, diphenylanthracene, and rubrerte. The amount of the radical polymerization initiator and/or the sensitizer, if added, is preferably 10 parts or less, more preferably 5 parts or less, even more preferably 0.1 to 3 parts, by mass per 100 parts by mass of the sum of the trifunctional (meth)acrylate compound and the liquid crystal compound.

Examples of the solvent include benzene, toluene, xylene, mesitylene, n-butylbenzene, diethylbenzene, tetralin, methoxybenzene, 1,2-dimethoxybenzene, ethylene glycol dimethyl ether, diethylene glycol dimethyl ether, acetone, methyl ethyl ketone, methyl isobutyl ketone, cyclopentanone, cyclohexanone, ethyl acetate, methyl lactate, ethyl lactate, ethylene glycol monomethyl ether acetate, propylene glycol monomethyl ether acetate, propylene glycol monoethyl ether acetate, γ-butyrolactone, 2-pyrrolidone, N-methyl-2-pyrrolidone, dimethylformamide, chloroform, dichloromethane, carbon tetrachloride, dichloroethane, trichloroethylene, tetrachloroethylene, chlorobenzene, t-butyl alcohol, diacetone alcohol, glycerol, monoacetylene, ethylene glycol, triethylene glycol, hexylene glycol, ethylene glycol monomethyl ether, ethyl cellosolve, and butyl cellosolve. The solvent may be a single compound or a mixture of compounds. A solvent having a boiling point of 60° to 250° C., particularly a solvent having a boiling point of 60° to 180° C. is preferred. A solvent whose boiling point is lower than 60° C. is liable to vaporize during application, resulting in thickness unevenness. A solvent whose boiling point is higher than 250° C. tends to remain even after solvent removal under reduced pressure or induce thermal polymerization when treated in high temperature, resulting in reduced aligning properties.

The polymerizable composition of the present invention may further contain an optically active compound to provide a polymer having inside a helical structure of the liquid crystal skeleton, namely, a fixed cholesteric liquid crystal phase. In this embodiment, the amount of the optically active compound to be added is preferably 0.1 to 100 parts, more preferably 1 to 50 parts, by mass per 100 pats by mass of the sum of the trifunctional (meth)acrylate compound and the liquid crystal compound (except the solvent). Examples of usable optically active compounds are [Formula 21] below.

[Formula 21]

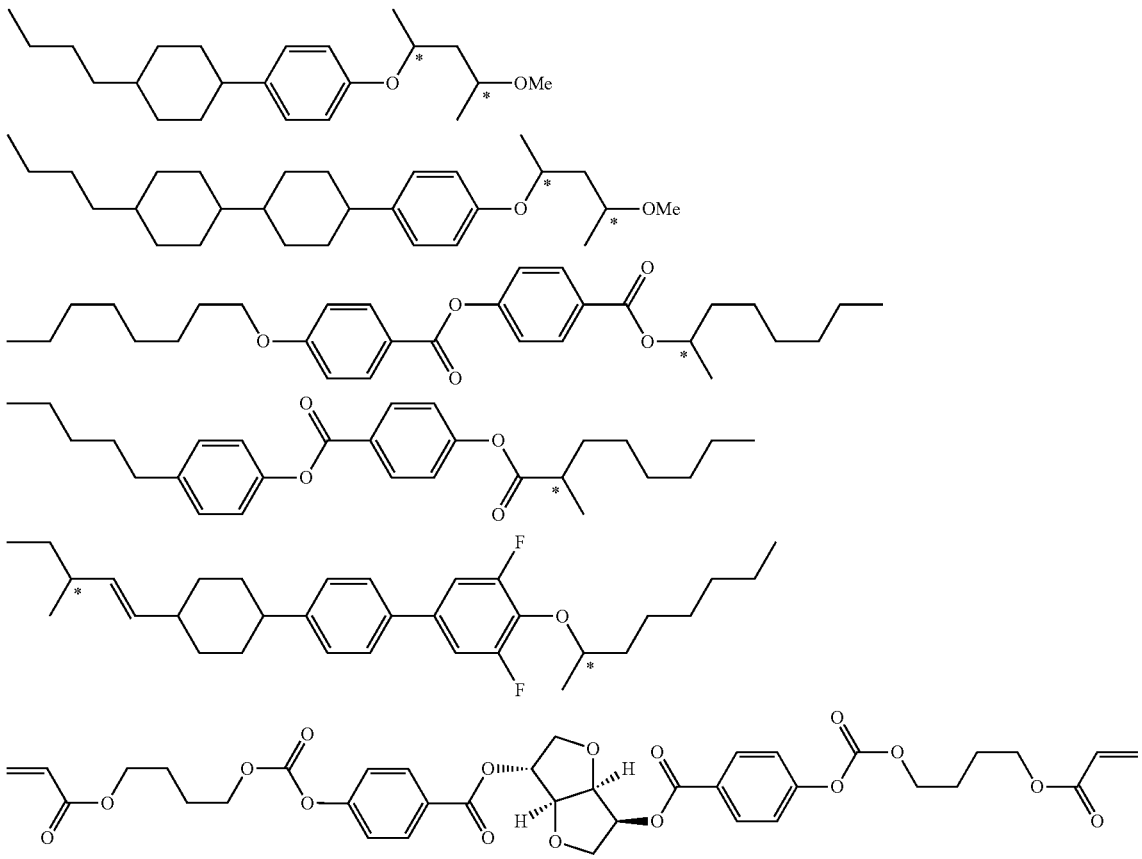

-continued

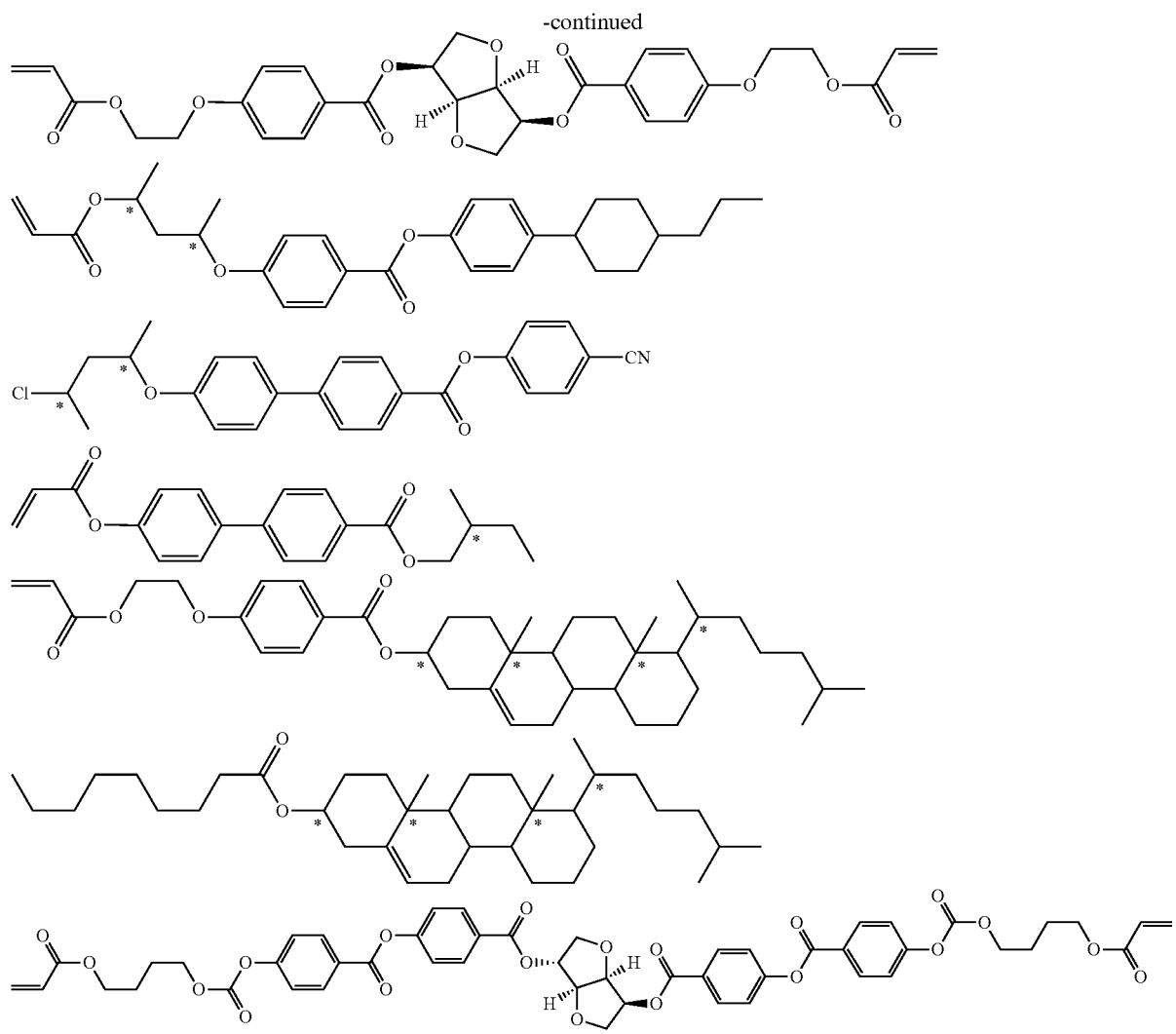

The polymerizable composition preferably contains a surfactant that produces an excluded volume effect over the interface with air. The surfactant is preferably selected from those effect in facilitating applying the polymerizable composition to a substrate or controlling the alignment of the liquid crystal phase. Such surfactants include quaternary ammonium salts, alkylamine oxides, polyamine derivatives, polyoxyethylene-polyoxypropylene condensates, polyethylene glycol and esters thereof, sodium laurylsulfate, ammonium laurylsulfate, amine laurylsulfates, alkyl-substituted aromatic sulfonates, alkylphosphates, perfluoroalkylsulfonates, perfluoroalkylcarboxylates, perfluoroalkyl ethylene oxide adducts, and perfluoroalkyltrimethylammonium salts. A preferred amount of the surfactant to be used depends on the kind of the surfactant, the compounding ratio of the composition, and the like but generally ranges from 0.001 to 5 parts by mass, more preferably 0.01 to 1 part by mass, per 100 parts by mass of the sum of the trifunctional (meth)acrylate compound of the invention and the liquid crystal compound.

Additives may be added to the polymerizable composition of the invention where needed to improve characteristics of the polymerizable composition, including functional compounds, such as storage stabilizers, antioxidants, ultraviolet absorbers, infrared absorbers, fine particles of organic, inorganic or other materials, and polymers.

The storage stabilizers serve to improve storage stability of the polymerizable composition, including hydroquinone, hydroquinone monoalkyl ethers, tert-butyl catechols, pyrogallols, thiophenols, nitro compounds, 2-naphtylamines, and 2-hydroxynaphthalenes. The amount of the storage stabilizer, if used, is preferably 1 part by mass or less, more preferably 0.5 parts by mass or less, per 100 parts by mass of the sum of the trifunctional (meth)acrylate compound of the invention and the liquid crystal compound.

Any known antioxidants may be used, including hydroquinone, 2,6-di(tert-butyl)-p-cresol, 2,6-di(tert-butyl)phenol, triphenyl phosphite, and trialkyl phosphites.

Any known UV absorbers may be used, including salicylic ester compounds, benzophenol compounds, benzotriazole compounds, cyanoacrylate compounds, and nickel complex salt compounds.

The fine particles may be used to adjust the optical (refractive index) anisotropy Δn or enhance the strength of the polymer film. The fine particles may be of organic, inorganic, or metallic materials. The particle size is preferably 0.001 to 0.1 μm, more preferably 0.001 to 0.05 μm, to prevent flocculation. The particle size distribution is preferably narrow. The amount of the particles, if used, is preferably 0.1 to 30 parts by mass per 100 parts by mass of the sum of the trifunctional (meth)acrylate compound of the invention and the liquid crystal compound.

The inorganic materials include ceramics, fluorophiogopite, fluorotetrasilicic mica, taeiniolite, fluorovermiculite, fluorohectorite, hectorite, saponite, stevensite, montmorillonite, beidellite, kaolinite, fraipontite, ZnO, $TiO_2$, $CeO_2$, $Al_2O_3$, $Fe_2O_3$, $ZrO_2$, $MgF_2$, $SiO_2$, $SrCO_3$, $Ba(OH)_2$, $Ca(OH)_2$, $Ga(OH)_3$, $Al(OH)_3$, $Mg(OH)_2$ and $Zr(OH)_4$. Fine particles having optical anisotropy exemplified by needle-like crystals of calcium carbonate may be used to adjust the optical anisotropy of the polymer. The organic materials include carbon nanotube, fullerene, dendrimer, polyvinyl alcohol, polymethacrylate, and polyimide.

The polymer as an additive may be added to adjust the electric characteristics or alignment characteristics of the polymer film. The polymer is preferably soluble in the above recited solvent. Examples of such a polymer include polyamide, polyurethane, polyurea, polyepoxide, polyester, and polyester polyol.

The above mentioned optional components (except the liquid crystal compound, the radical polymerization initiator, and the solvent) other than the trifunctional (meth)acrylate compound of the invention may be used appropriately with no particular limitation as long as the characteristics of the resulting polymer are not impaired. Preferably, the total amount of the optional components is not more than 10 parts per 100 parts by mass of the sum of the trifunctional (meth) acrylate compound and the liquid crystal compound.

The optically anisotropic element of the present invention is obtained by dissolving the polymerizable composition in a solvent, applying the resulting solution to a substrate, removing the solvent from the coating film in which the liquid crystal molecules of the polymerizable composition have been aligned, and then irradiating the coating film with energy rays to cause polymerization.

Examples of preferred substrates include, but are not limited to, plates of glass, polyethylene terephthalate, polycarbonate, polyimide, polyamide, polymethyl methacrylate, polystyrene, polyvinyl chloride, polytetrafluoroethylene, cellulose, silicone, or calcite, and a reflector plate. It is preferred to use the above described substrate which has formed thereon a polyimide alignment layer or a polyvinyl alcohol alignment layer.

The polymerizable composition solution can be applied to the substrate by any known coating techniques including curtain coating, extrusion coating, roll coating, spin coating, dipping, bar coating, spraying, slide coating, printing, and casting. The thickness of the polymer film is decided as appropriate to the end use, and is preferably 0.05 to 10 µm.

The liquid crystal molecules in the polymerizable composition are aligned by, for example, previously subjecting the substrate to an alignment treatment. Such an alignment treatment of the substrate is preferably carried out by providing a liquid crystal alignment layer, such as a polyimide alignment layer, a polyamide alignment layer, or a polyvinyl alcohol alignment layer, on the substrate, followed by rubbing the alignment layer or a like operation. Molecular alignment may also be achieved by applying a magnetic field or an electric field to the coating film of the polymerizable composition on the substrate.

The polymerizable composition can be polymerized by known processes using heat or electromagnetic radiation. Electromagnetic radiation-induced polymerization reactions include radical polymerization, anionic polymerization, cationic polymerization, coordination polymerization, and living polymerization. It is easy by electromagnetic radiation-induced photopolymerization to effect polymerization under a condition allowing the polymerizable composition to exhibit a liquid crystal phase. Crosslinking reaction in a magnetic field or an electric field is also preferred. The liquid crystal (co)polymer formed on the substrate may be used as such or, when needed, stripped off the substrate or transferred onto a different substrate.

Examples of the preferred light include ultraviolet light, visible light, and infrared light. Electromagnetic radiation, such as electron beams and X rays, may also be used. Usually, ultraviolet light or visible light is preferred. A preferred wavelength range is from 150 to 500 nm, more preferably from 250 to 450 nm, even more preferably 300 to 400 nm. Light sources include low pressure mercury lamps (e.g., bactericidal lamps, fluorescent chemical lamps, and black lights), high pressure discharge lamps (e.g., high pressure mercury lamps and metal halide lamps), and short arc discharge lamps (ultrahigh pressure mercury lamps, xenon lamps, and mercury xenon lamps), with ultrahigh pressure mercury lamps being preferred. The polymerizable composition may be irradiated with the light as emitted from a light source or a light ray of a specific wavelength or light rays of a specific wavelength range selected through a filter. A preferred irradiation energy density is 2 to 5000 $mJ/cm^2$, more preferably 10 to 3000 $mJ/cm^2$, even more preferably 100 to 2000 $mJ/cm^2$. A preferred illuminance is 0.1 to 5000 $mW/cm^2$, more preferably 1 to 2000 $mW/cm^2$. The temperature during irradiation may be decided so that the polymerizable composition may have a liquid crystal phase and is preferably 100° C. or lower. At temperatures higher than 100° C., thermal polymerization can occur, resulting in a failure to obtain satisfactory alignment.

The optically anisotropic element of the invention is used as a molded article with optical anisotropy. Such a molded article finds use as optical compensation films, including a retardation film (e.g., a ½-wave plate or a ¼-wave plate), a polarizer, a dichroic polarizing plate, a liquid crystal alignment layer, an antireflective film, a selectively reflecting film, and a viewing angle compensation film. The molded article also finds use as an optical lens, such as a liquid crystal lens or a microlens, and an information recording material, such as a PDLC type e-paper or a digital paper.

EXAMPLES

The present invention will now be illustrated in greater detail by way of Examples, Evaluation Examples, and Comparative Examples, but it should be understood that the invention is not deemed to be limited thereto. Examples 1-1 to 1-3 present the preparation of the trifunctional (meth)acrylate compounds of the invention.

Examples 2-1 and 2-2 and Comparative Examples 1-1 to 1-3 show the polymerizable compositions of the invention, comparative polymerizable compositions, and the making of optically anisotropic elements using the compositions. Evaluation Examples 1-1 and 1-2 and Comparative Evaluation Examples 1-1 to 1-3 present comparative evaluation of the optically anisotropic elements. Example 3 and Comparative Example 2 show polymerizable compositions of the invention containing an optically active compound, comparative polymerizable compositions containing an optically active compound, and the making of optically anisotropic elements using these compositions. Evaluation Example 2 and Comparative Evaluation Example 2 show comparative evaluation of the optically anisotropic elements.

Example 1-1

Preparation of Trifunctional (Meth)Acrylate Compound No. 1

Trifunctional (meth)acrylate compound No. 1 was prepared by the following procedures in accordance with reaction scheme of [Formula 22] below:

[Formula 22]

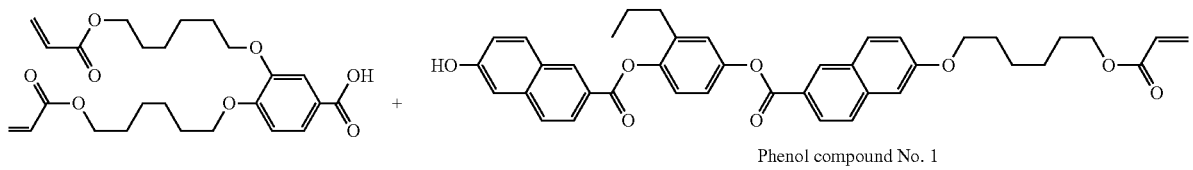

Phenol compound No. 1

↓

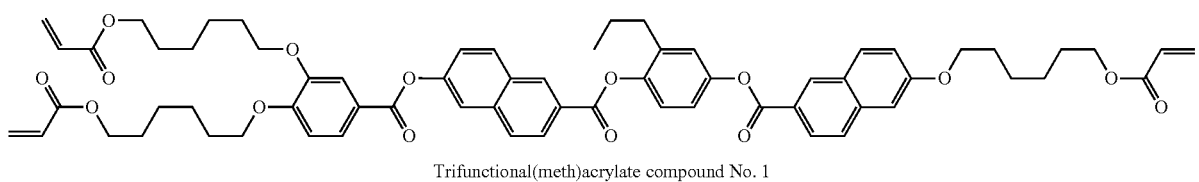

Trifunctional(meth)acrylate compound No. 1

In 17 ml of THF were dissolved 2.06 g (3.19 mmol) of phenol compound No. 1 and 2.21 g (4.78 mmol) of 3,4-di(6-acryloyloxyhexyloxy)benzoic acid, and 0.19 g (1.59 mmol) of 4-dimethylaminopyridine and 0.73 g (5.73 mmol) of diisopropylcarbodiimide were added to the solution while cooling with ice. The system was stirred at the same temperature for 10 minutes, followed by heating to room temperature, at which the stirring was continued for 3 hours. The solvent was evaporated under reduced pressure, and the residue was purified by silica gel column chromatography using a mixture of ethyl acetate and n-hexane as a developing solution to give a colorless transparent oily substance. Recrystallization from a mixed solvent of acetone and methanol followed by filtration yielded 2.8 g (81.6%) of a white solid. The white solid was identified to be the target trifunctional (meth)acrylate compound No. 1 by IR and $^1$H-NMR analyses, the results of which are shown below.

IR (neat): 2941, 2867, 1726, 1626, 1473, 1408, 1271, 1193, 1170, 1147, 1066, 811

$^1$H-NMR (400 MHz, CDCl$_3$): δ=8.83 (s, 1H), 8.71 (s, 1H), 8.25 (dd, 1H, J=7.3, 1.2 Hz), 8.16 (dd, 1H, J=7.3, 1.2 Hz), 8.08 (d, 1H, J=9.1 Hz), 7.96 (d, 1H, J=8.5 Hz), 7.90 (d, 1H, J=9.1 Hz), 7.88 (dd, 1H, J=8.5, 1.8 Hz), 7.81 (d, 1H, J=9.1 Hz), 7.78 (d, 1H, J=1.8 Hz), 7.71 (d, 1H, J=1.8 Hz), 7.47 (dd, 1H, J=8.8, 2.1 Hz), 7.26-7.15 (m, 5H), 6.96 (d, 1H, J=8.5 Hz), 6.44-6.36 (m, 3H), 6.17-6.07 (m, 3H), 5.84-5.77 (m, 3H), 4.23-4.07 (m, 12H), 2.64 (t, 2H, J=7.6 Hz), 1.95-1.85 (m, 6H), 1.79-1.65 (m, 8H), 1.63-1.42 (m, 12H), 0.95 (t, 3H, J=7.3 Hz)

The compound No. 1 was analyzed for thermal phase transition behavior on a differential scanning calorimeter (DSC 7 from Perkin Elmer) under conditions of a nitrogen atmosphere (50 mL/min), a heating rate of 5° C./min, and a heating temperature of from 25° C. upto 180° C. As a result, the compound exhibited the phase transition behavior shown in [FIG. 1]. The liquid crystal phase was identified by observing a sample sandwiched between glass plates and heated on a hot stage under a polarizing microscope.

Example 1-2

Preparation of Trifunctional (Meth)Acrylate Compound No. 2

Trifunctional (meth)acrylate compound No. 2 was prepared by the following procedures in accordance with reaction scheme of [Formula 23] below:

[Formula 23]

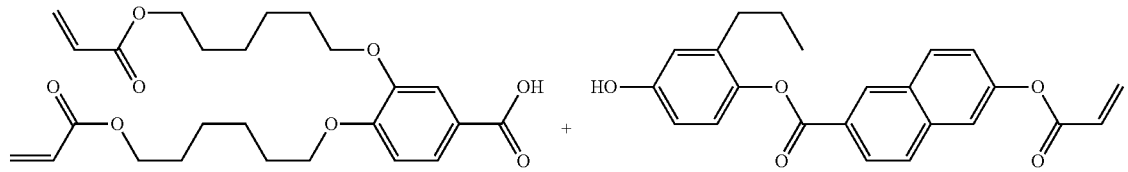

Phenol compound No. 2

↓

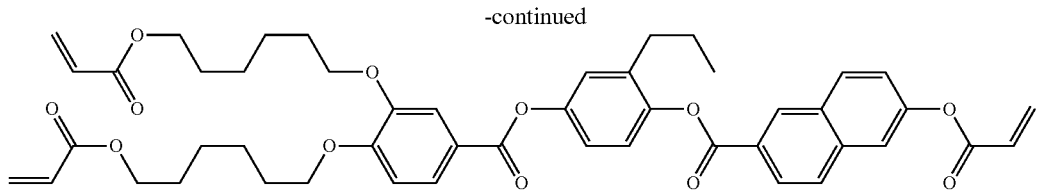

Trifunctional(meth)acrylate compound No. 2

A mixture of 2.7 g (23.8 mmol) of methanesulfonyl chloride and 37 g of THF was cooled to or below −20° C. while stirring. A mixture of 10 g (21.6 mmol) of 3,4-di(6-acryloyloxyhexyloxy)benzoic acid, 3.35 g (25.9 mmol) of diisopropylethylamine, and 37 g of THF was added thereto dropwise while maintaining the system at −20° C. or lower. After completion of the addition, the system was stirred at that temperature for 30 minutes. A microspatula of 4-dimethylaminopyridine and 3.35 g (25.9 mmol) of diisopropylethylamine were added thereto, and a mixture of 8.97 g (22.7 mmol) of phenol compound No. 2 and 37 g of THF was further added while maintaining the system at or below −10° C., followed by stirring at that temperature for 2 hours. The reaction mixture was washed with water, and 1% hydrochloric acid and toluene were added thereto to provide oil water separation. The organic layer was washed twice with water. The solvent was evaporated under reduced pressure, and the residue was purified by silica gel column chromatography using toluene as a developing solution. Recrystallization from methanol followed by filtration gave 4.5 g (25.4%) of a white solid. The white solid was identified to be the target trifunctional (meth)acrylate compound No. 2 by IR and $^1$H-NMR analyses, the results of which are shown below.

IR (KBr): 2937, 1717, 1632, 1598, 1516, 1495, 1474, 1410, 1295, 1265, 1207, 1189, 1160, 1078, 992, 812, 756 cm$^{-1}$ $^1$H-NMR (400 MHz, CDCl$_3$): δ=0.95 (t, 3H, J=7.3 Hz), 1.50-1.91 (m, 18H), 2.63 (q, 2H, J=7.6 Hz), 4.08-4.21 (m, 8H), 5.82-6.44 (m, 8H), 6.70 (d, 1H, J=17.1 Hz), 6.95 (d, 1H, J=8.5 Hz), 7.41-7.17 (m, 4H), 7.69 (d, 1H, J=1.8 Hz), 7.73 (d, 1H, J=1.8 Hz), 7.84-8.23 (m, 4H), 8.82 (s, 1H)

Figure 2:
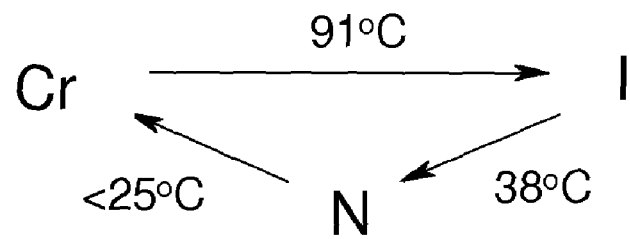
FIG. 2 schematically illustrates the thermal transition behavior of compound No. 2 prepared in Example 1-2.

The compound No. 2 was analyzed for thermal phase transition behavior in the same manner as in Example 1-1. As a result, the compound exhibited the phase transition behavior shown in [FIG. 2].

Example 1-3

Preparation of Trifunctional (Meth)Acrylate Compound No. 3

Trifunctional (meth)acrylate compound No. 3 was prepared by the following procedures in accordance with reaction scheme of [Formula 24] below:

[Formula 24]

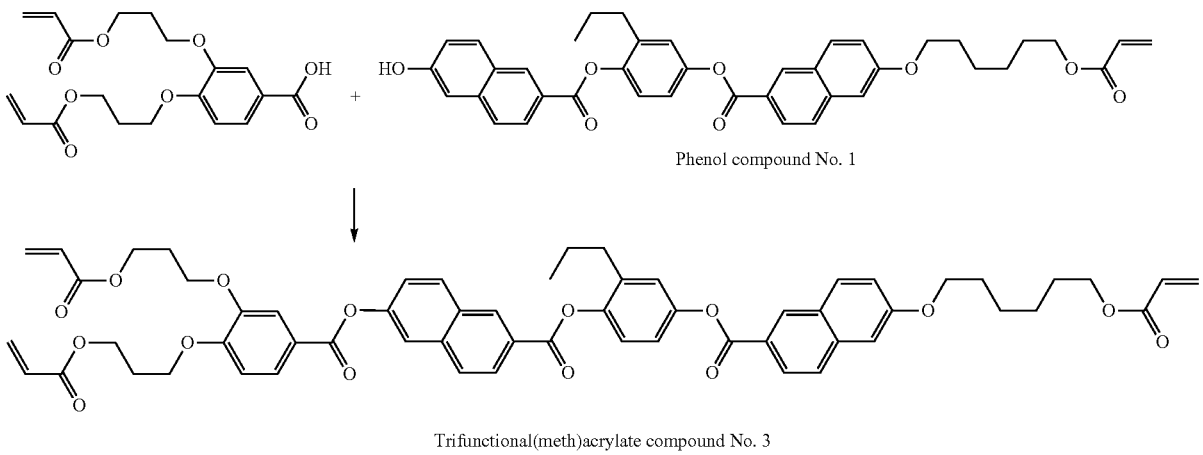

Phenol compound No. 1

Trifunctional(meth)acrylate compound No. 3

In 108 ml of THF were dissolved 9.20 g (14.2 mmol) of phenol compound No. 1 and 7.00 g (18.5 mmol) of 3,4-di(6-acryloyloxypropyloxy)benzoic acid, and 0.87 g (7.12 mmol) of 4-dimethylaminopyridine and 2.80 g (22.2 mmol) of diisopropylcarbodiimide were added to the solution while cooling with ice. The system was stirred at the same temperature for 30 minutes, followed by heating to room temperature, at which the stirring was continued for an additional 16 hour period. Acetone was added to the reaction mixture, and the precipitate thus formed was collected by filtration. The solvent was removed by evaporation under reduced pressure, and toluene was added thereto. The precipitate formed was collected by filtration, and the solvent was removed by evaporation under reduced pressure. The residue was purified by silica gel column chromatography using a mixture of ethyl acetate and n-hexane as a developing solution. The solvent was removed by evaporation under reduced pressure, and methanol was added to the residue, followed by stirring at room temperature overnight. The precipitate formed was collected by filtration and dried under reduced pressure at 40° C. for 1.5 hours to give 4.18 g of a colorless solid. Because the resulting solid still contained unreacted matter, the same procedures for synthesis described were repeated from the very beginning, except for starting with 0.31 g (0.81 mmol) of 3,4-di-(6-acryloyloxypropyloxy)benzoic acid. As a result, there was obtained 3.59 g of a colorless solid in a yield of 25.1%. The resulting colorless solid was identified to be the title trifunctional (meth)acrylate compound No. 3 by IR and $^1$H-NMR analyses, the results of which are shown below.

IR (neat): 2956, 2867, 1726, 1625, 1473, 1407, 1268, 1189, 1166, 1147, 1064 cm$^{-1}$ $^1$H-NMR (400 MHz, CDCl$_3$): δ=8.83 (s, 1H), 8.71 (s, 1H), 8.25 (dd, 1H, J=8.5, 1.2 Hz), 8.16 (dd, 1H, J=8.5, 1.8 Hz), 8.09 (d, 1H, J=9.1 Hz), 7.96 (d, 1H, J=8.5 Hz), 7.91-7.89 (m, 2H), 7.81 (d, 1H, J=8.5 Hz), 7.78 (d, 1H, J=2.4 Hz), 7.73 (d, 1H, J=1.8 Hz), 7.47 (dd, 1H, J=8.8, 2.1 Hz), 7.29 (d, 1H, J=8.5 Hz), 7.26-7.18 (m, 4H), 6.99 (d, 1H, J=8.5 Hz), 6.47-6.36 (m, 3H), 6.19-6.08 (m, 3H), 5.88-5.80 (m, 3H), 4.41 (t, 2H, J=6.1

[Formula 25]

Comparative compound No. 1

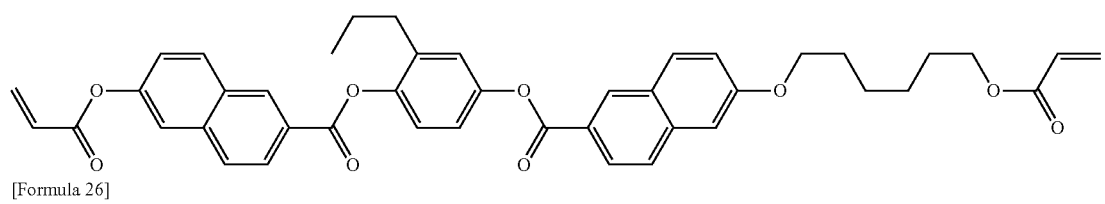

[Formula 26]

Comparative compound No. 2

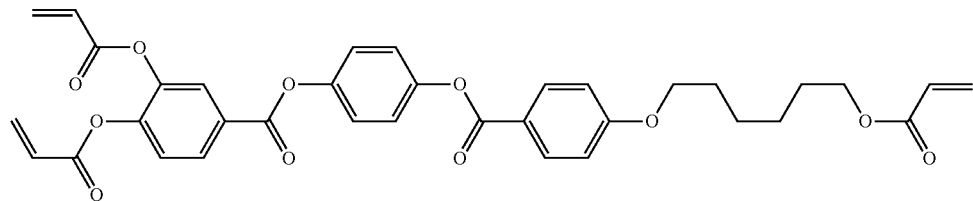

Hz), 4.41 (t, 2H, J=6.1 Hz), 4.24-4.16 (m, 6H), 4.13 (t, 2H, J=6.4 Hz), 2.64 (t, 2H, J=7.6 Hz), 2.32-2.20 (m, 4H), 1.95-1.86 (m, 2H), 1.79-1.65 (m, 4H), 1.63-1.46 (m, 4H), 0.95 (t, 3H, J=7.3 Hz)

Figure 3:
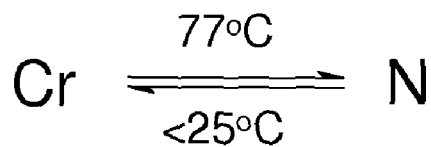
FIG. 3 schematically illustrates the thermal transition behavior of compound No. 3 prepared in Example 1-3.

The compound No. 3 was analyzed for thermal phase transition behavior in the same manner as in Example 1-1. As a result, the compound exhibited the phase transition behavior shown in FIG. 3.

The liquid crystal (nematic) to isotropic phase transition temperature of the compound is unclear because the compound undergoes thermal polymerization when heated to a high temperature. However, when it is heated to melt down to a liquid crystal state (nematic phase) and then cooled to room temperature (25° C.), it remains in the liquid crystal state without crystallization. Therefore, it is seen the compound is alone capable of retaining the liquid crystal state at 30° C. or lower.

Examples 2-1 and 2-2 and Comparative Examples 1-1 to 1-3

Preparation of Polymerizable Compositions and Optically Anisotropic Elements

Optically anisotropic elements were made from the trifunctional (meth)acrylate compounds of the invention and polymerizable compositions in accordance with the following procedures ([1] Preparation of polymerizable composition solution, and [2] Application to substrate and curing).

[1] Preparation of Polymerizable Composition Solution

Polymerizable composition solutions were prepared as follows using trifunctional (meth)acrylate compound No. 1 and comparative compound Nos. 1 and 2 according to the formulation shown in [Table 1] below. In 4.0 g of cyclopentanone (solvent) was dissolved 1.0 g of each polymerizable compound (composition), and 0.03 g of a radical polymerization initiator (ADEKAOPTOMER N-1919, from ADEKA Corp.) was added and completely dissolved therein. The mixture was filtered through a filter having a pore size of 0.45 μm to prepare a polymerizable solution.

[2] Application to Substrate and Curing

A glass plate having polyimide applied thereto and rubbed was prepared. The polymerizable composition solution prepared in [1] above was applied to the substrate with a spin coater. The speed and time of rotation of the spin coater were adjusted so as to give a coating film thickness of about 1.0 μm. After application, the coating film was dried on a hot plate at 100° C. for 3 minutes, allowed to cool at room temperature for 5 minutes, and then irradiated with light of a high pressure mercury lamp to give an energy of 300 mJ/cm$^2$ to cure to form an optically anisotropic film.

Evaluation Example 1-1 and 1-2 and Comparative Evaluation Examples 1-1 to 1-3

The optically anisotropic films obtained in Examples above were evaluated for physical properties (i.e., alignment uniformity and heat resistance) as follows. The results obtained are shown in [Table 1] below.

<Alignment Uniformity>

Uniformity of the molecular alignment in the optically anisotropic film was evaluated using a polarizing microscope. A sample film was mounted on the rotating stage between crossed polarizers, and the stage was rotated to observe the alignment state of the film and to evaluate the alignment uniformity. A sample showing uniform alignment was rated "A". A sample showing alignment but suffering from non-uniformity or surface whitening was rated "B". A sample showing an alignment defect due to, e.g., crystallization was rated "C".

<Heat Resistance>

The optically anisotropic film was heated in an oven at 150° C. for 30 minutes. The retardation (R) of the film was measured before and after the heating to determine the retardation reduction (%) due to the heating. A sample showing a reduction of more than 10% was rated "C". A sample showing a reduction of 5% to 10% was rated "B". A sample showing a reduction of less than 5% was rated "A". A sample showing a reduction of less than 1% was rated "AA". The retardation R was determined in accordance with the Senarmont method using a polarizing microscope at room temperature (25° C.) at a wavelength of 546 nm.

TABLE 1

|  | Example No. | | Comparative Example No. | | |
|---|---|---|---|---|---|
|  | 2-1 | 2-2 | 1-1 | 1-2 | 1-3 |
| Polymerizable Composition (a total of 100 parts by mass): | | | | | |
| Trifunctional (meth)acrylate Compound No. 1 | 100 | 50 | 0 | 0 | 0 |
| Comparative Compound No. 1 | 0 | 50 | 100 | 0 | 50 |
| Comparative Compound No. 2 | 0 | 0 | 0 | 100 | 50 |
| Physical Properties: | | | | | |
| Alignment Uniformity | A | A | A | C | B** |
| Heat Resistance | AA (<1) | AA (<1) | B (8.9) | * (*) | C (11.1) |

TABLE 1-continued

|  | Example No. | | Comparative Example No. | | |
|---|---|---|---|---|---|
|  | 2-1 | 2-2 | 1-1 | 1-2 | 1-3 |
| (Retardation reduction; %) | | | | | |

Note:
*: After the cure, the surface of the film exhibited whitening due to crystallization. Retardation was unmeasurable.
**: An alignment defect (disclination) was observed in part under a polarizing microscope.

It is apparent from the results in [Table 1] that the optically anisotropic elements obtained from the polymerizable compositions of the invention exhibit uniform alignment and excellent heat resistance, whereas those from only the comparative compound(s) have disturbed alignment or poor heat resistance, proving the usefulness of the trifunctional (meth)acrylate compound of the invention.

Example 3 and Comparative Example 2

Preparation of Polymerizable Composition and Optically Anisotropic Element Containing Optically Active Compound Optically anisotropic elements were made from the trifunctional (meth)acrylate compound of the invention and polymerizable compositions in accordance with the following procedures.

[1] Preparation of Polymerizable Composition Solution

Polymerizable composition solutions were prepared as follows using trifunctional (meth)acrylate compound No. 2, comparative compound No. 2, and liquid crystal compound No. 1 according to the formulation shown in [Table 2] below.

In 2.0 g of cyclopentanone (solvent) were dissolved 0.95 g of the polymerizable composition shown and 0.05 g of optically active compound No. 1, and 0.03 g of a radical polymerization initiator (ADEKAOPTOMER N-1919, from ADEKA Corp.) was added and completely dissolved therein. The mixture was filtered through a filter having a pore size of 0.45 μm to prepare a polymerizable solution.

[Formula 27]

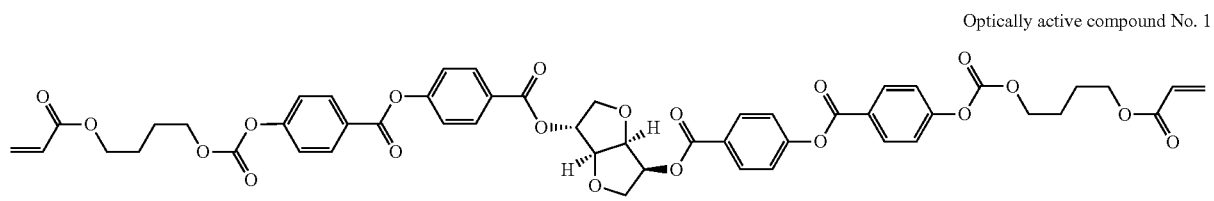

Optically active compound No. 1

[Formula 28]

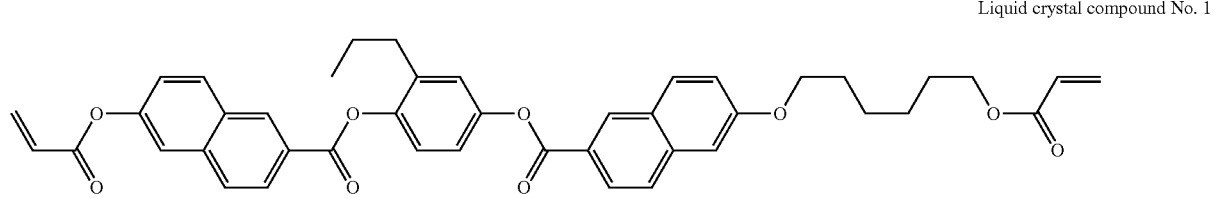

Liquid crystal compound No. 1

[2] Application to Substrate and Curing

A glass plate having polyimide applied thereto and rubbed was prepared. The polymerizable solution prepared in [1] above was applied to the substrate with a spin coater. The speed and time of rotation of the spin coater were adjusted so as to give a coating film thickness of about 2.0 μm. After application, the coating film was dried on a hot plate at 100° C. for 3 minutes, allowed to cool at room temperature for 3 minutes, and then irradiated with light of a high pressure mercury lamp to give an energy of 300 mJ/cm² to cure to form an optically anisotropic film.

Evaluation Example 2 and Comparative Evaluation Examples 2

The optically anisotropic films obtained in Examples were evaluated for physical properties (alignment uniformity and selective reflection wavelength) as follows. The results obtained are shown in [Table 2] below.

<Alignment Uniformity>

Uniformity of molecular alignment of the optically anisotropic film was evaluated using a polarizing microscope. A sample film was mounted on the rotating stage between crossed polarizers, and the stage was rotated to observe the alignment state of the film and to evaluate the alignment uniformity. A sample showing uniform selective reflection with no alignment defects observed was rated "A". A sample showing selective reflection but with an oily streak defect observed was rated "B". A sample showing crystallization or alignment non-uniformity was rated "C".

<Selective Reflection Wavelength Measurement>

Reflective indices of the optically anisotropic film were measured in a wavelength range of 400 to 800 nm at 25° C. using a spectrophotometer (U-3010, from Hitachi High-Technologies Corp.) equipped with a 5° specular reflection accessory to obtain the central wavelength (λ) of the selective reflection wavelength band.

TABLE 2

|  | Example 3 | Comparative Example 2 |
|---|---|---|
| Polymerizable Composition (a total of 100 parts by mass): | | |
| Trifunctional (meth)acrylate Compound No. 2 | 47.5 | |
| Comparative Compound No. 2 | | 47.5 |
| Liquid Crystal Compound No. 1 | 47.5 | 47.5 |
| Optically Active Compound No. 1 | 5 | 5 |
| Physical Properties: | | |
| Alignment Uniformity | A | C (surface whitening) |
| Selective Reflection Wavelength/ $\lambda_{max}$ (nm) | good (reddish orange)/621 | bad |

It is seen from the above results that the optically anisotropic film obtained from the polymerizable composition of the invention exhibits uniform selective reflection in a specific wavelength band and no alignment defects, whereas the film obtained from the comparative composition showed surface whitening. It is thus obvious that the optically anisotropic film prepared using the trifunctional (meth)acrylate compound of the invention is useful particularly as an optical film.

INDUSTRIAL APPLICABILITY

The polymerizable composition containing the trifunctional (meth)acrylate compound of the invention is excellent in solvent solubility and compatibility with other liquid crystal compounds. The optically anisotropic element of the invention, which is obtained by photopolymerizing the polymerizable composition controlling alignment while it is in the liquid crystal state, is excellent in alignment controllability, optical characteristics, and the like and useful as an optical material.

The invention claims is:

1. A trifunctional (meth)acrylate compound represented by general formula (I):

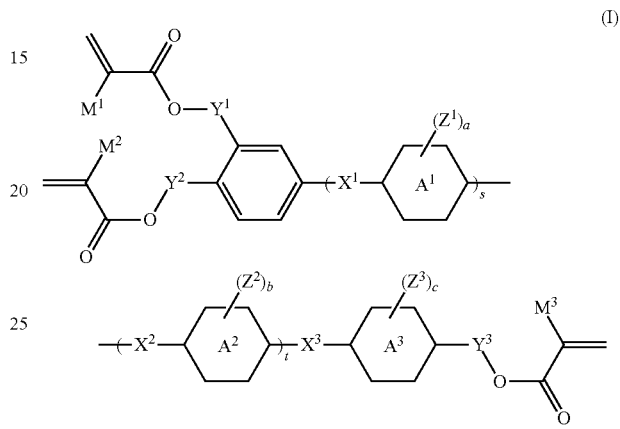

wherein:

$M^1$, $M^2$, and $M^3$ each independently represent a hydrogen atom, a methyl group, or a halogen atom;

ring $A^1$, ring $A^2$, and ring $A^3$ each independently represent a benzene ring, a cyclohexane ring, a cyclohexene ring, a naphthalene ring, a decahydronaphthalene ring, a tetrahydronaphthalene ring, or a phenanthrene ring, the —CH= moiety of each of said rings is optionally displaced with —N= or the —CH²— moiety of each of said rings is optionally displaced with —S— or —O—;

at least one of ring $A^1$, ring $A^2$, and ring $A^3$ is a naphthalene ring;

$Z^1$, $Z^2$, and $Z^3$ each independently represent an alkyl group having 1 to 6 carbon atoms, optionally substituted with a halogen atom or a cyano group, and optionally having a methylene group thereof interrupted by —O— or —CO—;

$X^1$, $X^2$, and $X^3$ each independently represent a single bond, —COO—, —OCO—, —(CH$_2$)$_p$—, —CH=CH—, —(CH$_2$)$_p$O—, —O(CH$_2$)$_p$—, —CH=CHCH$_2$O—, —OCH$_2$CH=CH—, —C≡C—, —(CH$_2$)$_p$COO—, —OCO(CH$_2$)$_p$—, —(CH$_2$)$_p$OCO—O—, —OCO—O (CH$_2$)$_p$—, —(CH$_2$)$_q$O (CH$_2$)$_r$O—, or —O(CH$_2$)$_q$O (CH$_2$)$_r$—;

$Y^1$ and $Y^2$ each independently represent -L$^1$-, -L$^1$O—, -L$^1$O—CO—, -L$^1$CO—O—, or -L$^1$O—CO—O—;

$Y^3$ represents a single bond, -L$^2$-, —OL$^2$-, —O—COL$^2$-, —CO—OL$^2$-, or —O—CO—OL$^2$-;

$L^1$ and $L^2$ each independently represent an alkylene group having 1 to 8 carbon atoms optionally interrupted by one to three —O— linkages;

a, b, and c represent the numbers of substituents on ring $A^1$, ring $A^2$, and ring $A^3$, respectively, each independently being an integer of $(2u+2)$ or smaller, wherein u is the number of 6-membered rings in each respective ring $A^1$, ring $A^2$, ring $A^3$;

at least one of a, b, and c is an integer of 1 or greater;

p represents an integer of 1 to 8;

q and r each independently represent an integer of 1 to 3; and s and t each independently represent 0 or 1, provided that s+t≧1.

2. The trifunctional (meth)acrylate compound according to claim 1, wherein each of ring $A^1$, ring $A^2$, and ring $A^3$ independently is a benzene ring or a naphthalene ring.

3. The trifunctional (meth)acrylate compound according to claim 1, wherein each of $X^1$, $X^2$, and $X^3$ independently is —COO— or —OCO—.

4. The trifunctional (meth)acrylate compound according to claim 1, wherein ring $A^3$ is a naphthalene ring.

5. The trifunctional (meth)acrylate compound according to claim 1, which is alone capable of retaining a liquid crystal phase at or below 30° C.

6. A polymerizable composition comprising the trifunctional (meth)acrylate compound according to claim 1.

7. The polymerizable composition according to claim 6, further comprising an optically active compound and exhibiting a cholesteric liquid crystal phase.

8. The polymerizable composition according to claim 6, further comprising a radical polymerization initiator.

9. An optically anisotropic element obtained by photopolymerizing the polymerizable composition according to claim 6.

10. An optical film for display devices comprising the optically anisotropic element according to claim 9.

11. The trifunctional (meth)acrylate compound according to claim 2, wherein each of $X^1$, $X^2$, and $X^3$ independently is —COO— or —OCO—.

12. The trifunctional (meth)acrylate compound according to claim 2, wherein ring $A^3$ is a naphthalene ring.

13. The trifunctional (meth)acrylate compound according to claim 3, wherein ring $A^3$ is a naphthalene ring.

14. The trifunctional (meth)acrylate compound according to claim 2, which is alone capable of retaining a liquid crystal phase at or below 30° C.

15. The trifunctional (meth)acrylate compound according to claim 3, which is alone capable of retaining a liquid crystal phase at or below 30° C.

16. The trifunctional (meth)acrylate compound according to claim 4, which is alone capable of retaining a liquid crystal phase at or below 30° C.

17. A polymerizable composition comprising the trifunctional (meth)acrylate compound according to claim 2.

18. A polymerizable composition comprising the trifunctional (meth)acrylate compound according to claim 3.

19. A polymerizable composition comprising the trifunctional (meth)acrylate compound according to claim 4.

20. A polymerizable composition comprising the trifunctional (meth)acrylate compound according to claim 5.

* * * * *